US007348175B2

(12) United States Patent
Vilendrer et al.

(10) Patent No.: US 7,348,175 B2
(45) Date of Patent: Mar. 25, 2008

(54) BIOREACTOR WITH PLURALITY OF CHAMBERS FOR CONDITIONING INTRAVASCULAR TISSUE ENGINEERED MEDICAL PRODUCTS

(75) Inventors: Kent Vilendrer, Eden Prairie, MN (US); Troy Nickel, St. Louis Park, MN (US)

(73) Assignee: St3 Development Corporation, Eden Prairie, MN (US)

( * ) Notice: Subject to any disclaimer, the term of this patent is extended or adjusted under 35 U.S.C. 154(b) by 378 days.

(21) Appl. No.: 10/371,175

(22) Filed: Feb. 19, 2003

(65) Prior Publication Data

US 2003/0199083 A1    Oct. 23, 2003

Related U.S. Application Data

(60) Provisional application No. 60/429,583, filed on Nov. 27, 2002, provisional application No. 60/364,500, filed on Mar. 15, 2002.

(51) Int. Cl.
| | |
|---|---|
| A01N 1/00 | (2006.01) |
| A01N 1/02 | (2006.01) |
| C12M 1/00 | (2006.01) |
| C12M 3/00 | (2006.01) |
| A61F 2/04 | (2006.01) |

(52) U.S. Cl. ............... 435/284.1; 435/289.1; 435/299.1; 435/297.2; 435/304.2; 435/394; 435/286.5; 623/915; 623/916; 623/921; 600/36

(58) Field of Classification Search ............ 435/284.1, 435/289.1, 299.1, 297.2, 304.2, 394, 286.5; 623/915, 916, 921; 600/36
See application file for complete search history.

(56) References Cited

U.S. PATENT DOCUMENTS

| 5,665,594 A | 9/1997 | Schwarz et al. ............. 435/394 |
| 5,670,708 A | 9/1997 | Vilendrer ....................... 73/37 |
| 5,792,603 A | 8/1998 | Dunkelman et al. ......... 435/1.2 |
| 5,843,766 A | 12/1998 | Applegate et al. ....... 435/284.1 |
| 5,846,828 A | 12/1998 | Peterson et al. ............ 435/399 |
| 5,902,937 A * | 5/1999 | Amrani et al. ................ 73/856 |

(Continued)

FOREIGN PATENT DOCUMENTS

| EP | 1186653 | 3/2002 |
| WO | WO-97/39624 | 10/1997 |
| WO | WO-01/68800 | 9/2001 |

OTHER PUBLICATIONS

Peng, Xinqi, et al., "In Vitro System to Study Realistic Pulsatile Flow and Stretch Signaling in Cultured Vascular Cells", *Am J Physiol Cell Physiol*, vol. 279 (2000); pp. C797-C805.

(Continued)

*Primary Examiner*—Gladys J P Corcoran
*Assistant Examiner*—Nathan A. Bowers
(74) *Attorney, Agent, or Firm*—Nikolai & Mersereau, P.A.; C. G. Nersereau

(57) ABSTRACT

A microprocessor controlled and instrumented bioreactor for conditioning intravascular tissue engineered medical products. One bioreactor design including an integrated pump to provide a relatively small volume of fluid nutrient. The microprocessor control providing measurement and control of the fluid flow and tissue displacement and subsequent determination of material properties. One design includes a flexible joint providing motion of the treated tissue in the axial, bending and torsional direction.

43 Claims, 27 Drawing Sheets

U.S. PATENT DOCUMENTS

| | | | |
|---|---|---|---|
| 6,001,643 A * | 12/1999 | Spaulding | 435/298.2 |
| 6,008,049 A | 12/1999 | Naughton et al. | |
| 6,060,306 A | 5/2000 | Flatt et al. | 435/297.2 |
| 6,121,042 A | 9/2000 | Peterson et al. | 435/284.1 |
| 6,171,812 B1 | 1/2001 | Smith et al. | |
| 6,174,719 B1 * | 1/2001 | Elizondo et al. | 435/284.1 |
| 6,210,957 B1 * | 4/2001 | Carpentier et al. | 435/284.1 |
| 6,357,303 B1 | 3/2002 | Smith et al. | |
| 6,416,995 B1 * | 7/2002 | Wolfinbarger | 435/289.1 |
| 6,632,658 B1 | 10/2003 | Schoeb | |
| 6,827,682 B2 * | 12/2004 | Bugge et al. | 600/16 |
| 2001/0043918 A1 * | 11/2001 | Masini et al. | 424/93.7 |
| 2002/0037580 A1 | 3/2002 | Schoeb | |
| 2002/0062151 A1 * | 5/2002 | Altman et al. | 623/13.17 |
| 2003/0064358 A1 * | 4/2003 | Elson et al. | 435/4 |
| 2004/0219659 A1 * | 11/2004 | Altman et al. | 435/284.1 |
| 2005/0019748 A1 * | 1/2005 | Ochi et al. | 435/4 |
| 2006/0223047 A1 * | 10/2006 | Dancu et al. | 435/1.2 |

OTHER PUBLICATIONS

Wittstein, Ilan S., et al., "Opposite Effect of Pressurized Steady Versus Pulsatile Perfusion on Vascular Endothelial Cell Cytosolic pH", *Circulation Research*, vol. 86 (2000; pp. 1230-1236.

Vilendrer, Kent., et al. ,"Instrumented/ServoControlled Bioreactor for Conditioning Intravascular Tissue Engineered Medical Products (TEMPS)", U.S. Appl. No. 60/364,500, filed Mar. 15, 2002; 41 pages.

Vilendrer, Kent.,et al. ,"Bioreactor With Plurality of Chambers for Conditioning Intravascular Tissue Engineered Medical Products", U.S. Appl. No. 60/429,583, filed Nov. 27, 2002; 61 pages.

Altman, Gregory H., et al., "Advanced Bioreactor with Controlled Application of Multi-Dimensional Strain for Tissue Engineering", *Journal of Biomechanical Engineering*, vol. 124,(Dec. 2002),742-749.

Sodian, R , et al., "New Pulsatile Bioreactor For Fabrication of Tissue-Engineered Patches", *Journal Of Biomedical Materials Research*, vol. 58, No. 4, (2001),401-405.

* cited by examiner

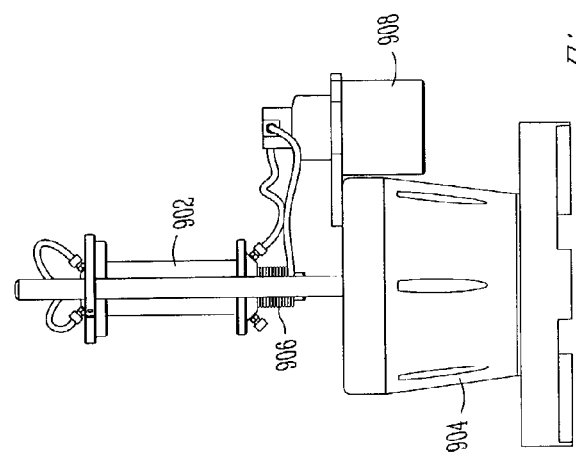
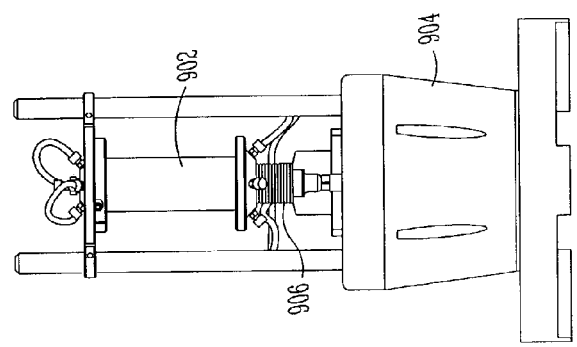
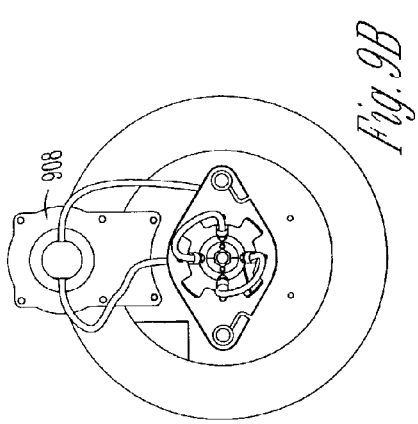
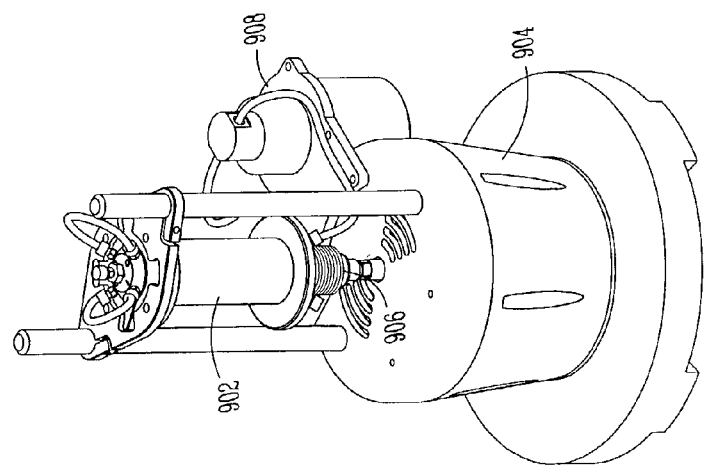

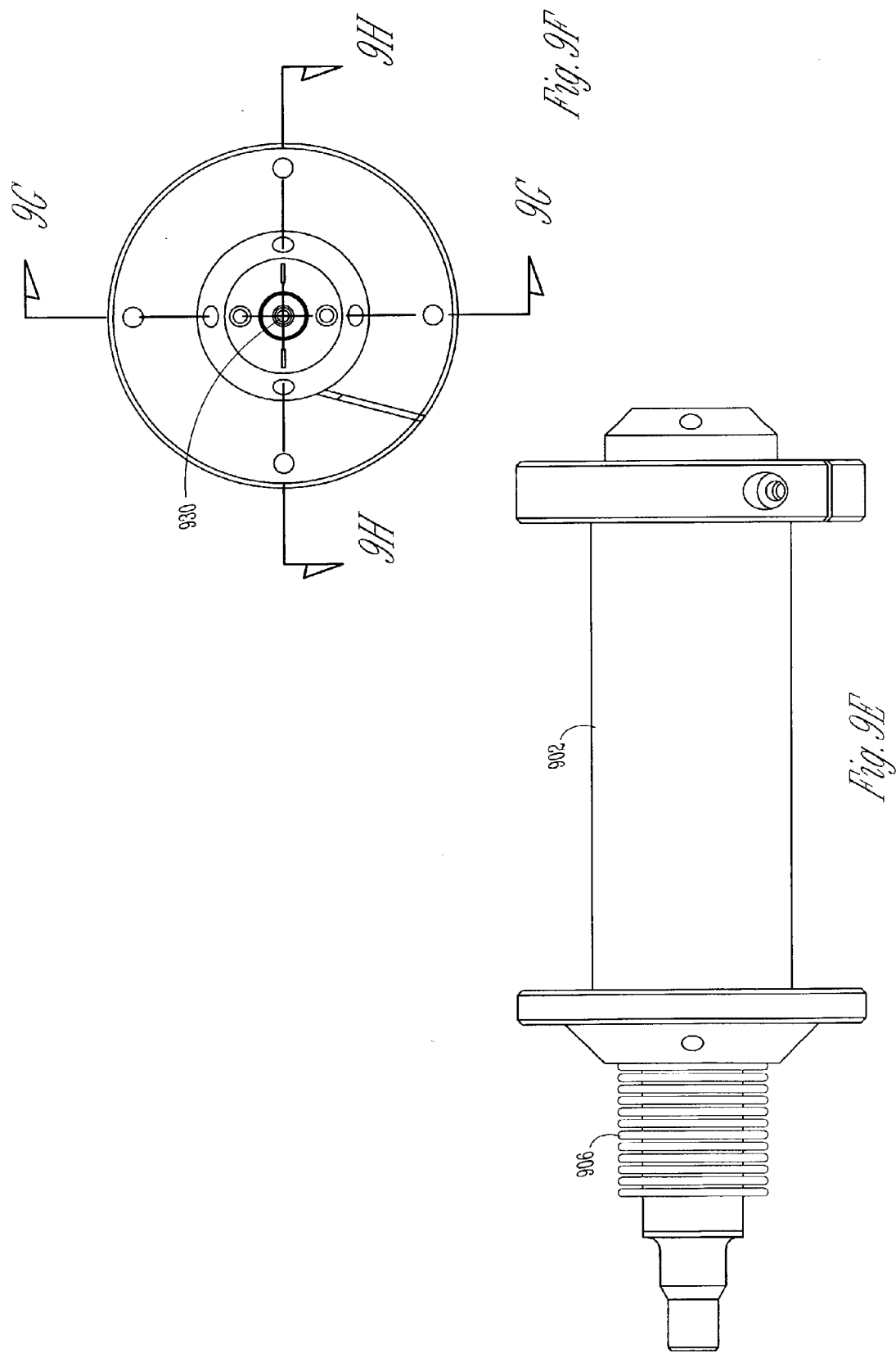

BIOREACTOR WITH PLURALITY OF CHAMBERS FOR CONDITIONING INTRAVASCULAR TISSUE ENGINEERED MEDICAL PRODUCTS

RELATED APPLICATIONS

This application claims priority under 35 U.S.C. 119(e) from U.S. Provisional Patent Application Ser. No. 60/364,500 filed Mar. 15, 2002, and from U.S. Provisional Patent Application Ser. No. 60/429,583 filed Nov. 27, 2002, which applications are incorporated herein by reference.

FIELD OF THE INVENTION

This disclosure relates to method and apparatus for growing and conditioning intravascular tissue engineered medical products and in particular to method and apparatus for an instrumented and servocontrolled bioreactor for conditioning intravascular tissue engineered medical products.

BACKGROUND

The replacement or repair of diseased vessels with natural synthetic vascular grafts is one treatment for certain types of intravascular disease. For coronary bypass surgery, the autologous saphenous vein remains the graft of choice for its non-thrombogenic flow surface, ability to be healed by the host as well as its strength and elasticity. Efforts to create a suitable synthetic small diameter vascular graft have been largely unsuccessful.

Likewise, man-made medical devices have been used to replace heart valves and repair other intravascular complications. These devices are typically made from metals (stainless steel, nickel titanium alloys, carbon, fiber) and fabric (PTFE, Dacron, carbon fiber) that are foreign to the body. The use of them requires special blood thinning medication that can lead to further health complications. Additionally, the devices are fixed form and do not conform to the body as the patient grows from childhood to adulthood thus necessitating multiple surgeries.

There are some areas (i.e., venous valves) where medical device designs offer low patency and the only means of repair is through reconstructive surgery or transplantation.

Researchers have sought to develop living alternatives to the traditional "man-made" medical devices. These tissue engineered medical products (TEMPs) use the patients own cells to create a replacement device that can be nurtured and grown once they are implanted. Through design, specification, and fabrication of cells, biomaterials, or biomolecules, it is hoped that TEMPs will play a major role in future heart valve replacement, cardiovascular bypass surgery, venous valve repair and other intravascular surgeries.

There is a need in the art for method and apparatus for growing and conditioning tissue engineered intravascular medical products.

SUMMARY

The present invention addresses the need in the art for method and apparatus for growing and conditioning tissue and other needs which will be appreciated by those of skill in the art upon reading and understanding the teachings of the present invention.

The present subject matter relates to a bioreactor for conditioning tissue in various embodiments including a bioreactor chamber, the bioreactor chamber including at least one clamp for holding the tissue, circulation means to provide fluid nutrient flow across the surface of the tissue; and microprocessor control means for measuring fluid flow in the bioreactor chamber and for measuring response of the tissue, wherein the microprocessor control means provides real time monitoring and control of conditions for the tissue within the bioreactor chamber, as described in the detailed description and recited in the claims.

Also described are different embodiments of a bioreactor for treatment of tissue, including a plurality of ports, a chamber for holding the tissue, dynamic pump means for providing dynamic pumping of fluids to the tissue, mean pump means for providing a mean flow of fluids to the tissue, a first manifold connected to the chamber at one end and a flexible joint connected to the other end, a second manifold connected to the flexible joint, actuating means for actuating the second manifold with respect to the first manifold, sensor means for measuring various pressures and temperatures within the bioreactor; and control means for controlling fluid flows and motion of the actuating means, as described in the detailed description and recited in the claims.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

FIGS. 9A, 9B, 9C, and 9D show different views of a tissue valve conditioner, according to one embodiment of the present invention.

FIGS. 9E, 9F, 9G, and 9H show different views of a bioreactor chamber of the tissue valve conditioner of FIGS. 9A-9D, according to one embodiment of the present invention.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

The present disclosure relates to method and apparatus for an instrumented and servocontrolled bioreactor for conditioning intravascular tissue engineered medical products (TEMPS). This detailed description incorporates by reference in its entirety U.S. Pat. No. 5,670,708 to Vilendrer, issued Sep. 23, 1997, entitled High Frequency "Intravascular Prosthesis Fatigue Tester." This detailed description also incorporates by reference in its entirety U.S. Provisional Patent Application Ser. No. 60/364,500 filed Mar. 15, 2002.

Intravascular TEMPs are typically comprised of a collagen matrix that is populated with multiple layers of cells including endothelial, smooth muscle cells and fibroblasts. The matrix provides a structure that the cells can grow on. In order for the cells to grow, they must be exposed to a nutrient environment. An environment where the cells could grow and multiply rapidly is desirable. Furthermore, properly imparting stresses into the cells promotes faster growth, orientation and strength. For example, fluid shear stresses cause endothelial (inner wall of the vessel) cells to orient in a direction that coincides with the blood flow just as they are oriented in vivo. Pulsatile pressure induced into the vessel causes the muscle cells to orient themselves circumferentially as they would in vivo.

Figure 1A:
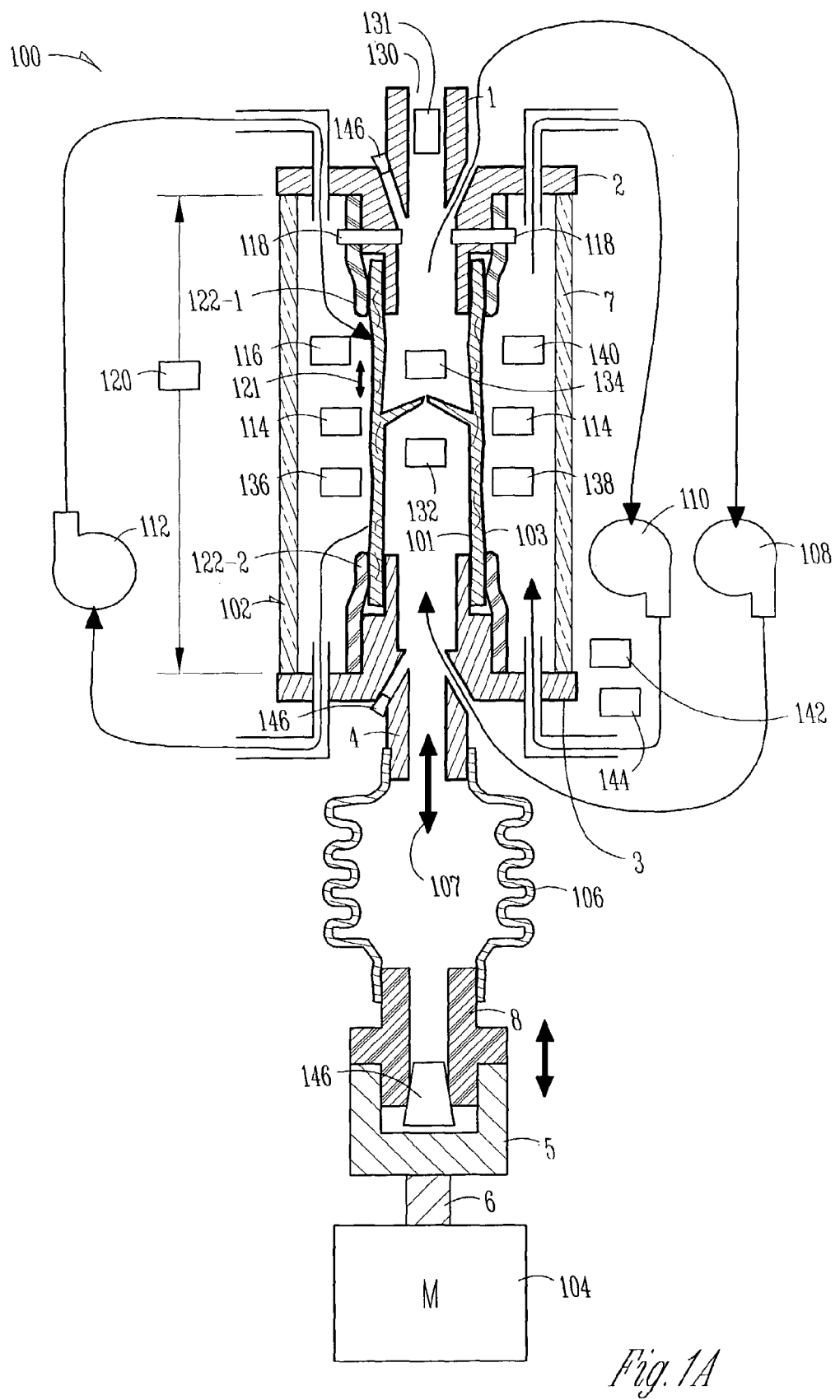
FIG. 1A is one embodiment of a microprocessor controlled bioreactor according to one embodiment of the present invention.

FIG. 1A provides one embodiment of a servocontrolled bioreactor configuration 100 for growing and conditioning intravascular tissue engineered medical products, including, but not limited to, heart valves, coronary arteries, venous valves and other devices. In the example of FIG. 1A it is noted that the tissue engineered prosthesis (bioprosthesis) 101 is valved. In other embodiments the bioprosthesis 101 is not valved, since the bioprosthesis 101 does not have to be valved to operate in accordance with the system.

The system 100 shown in FIG. 1A includes a bioreactor chamber assembly 102 and a computer controlled motorized frame driven by a linear motor 104. The linear motor 104 drives a dynamic pump 106 to produce a dynamic pump flow as demonstrated by arrow 107. This embodiment also includes mean flow pumps 108, 110, and 112, which provide a mean pump flow as shown by the arrows from the mean flow pumps 108, 110, and 112. This embodiment includes, but is not limited to, four transducers 114, 116, 118, and 120. The transducers provide measurements including, but not limited to, fluid flow velocities, and compliance (diametric displacement) of the bioprosthesis 101 in response to flow pulses, load measurement along the longitudinal axis of the bioprosthesis 101 and axial displacement (or strain) of the bioprosthesis 101.

The dynamic pump may be different designs. In different embodiments, the dynamic pump includes a linear motor, servomotor, voice coil, piezo, stepper motor, solenoid, pneumatic, servohydraulic, cam driven, and rotary crank driven designs. Other pumps are possible without departing from the scope of the present teachings.

In one embodiment, transducer 114 includes a laser micrometer. In one application, the laser micrometer is used to measure diametric deflection of the bioprosthesis 101. Additional sensor embodiments exist. In one embodiment, transducer 114 includes an ultrasonic measurement system. In one embodiment, transducer 114 includes a piezoelectric measurement system. In one embodiment, transducer 114 includes an optical measurement system. In one embodiment, transducer 114 includes an infrared measurement system. In one embodiment, transducer 114 incorporates a triangularization method for determining motion of the bioprosthesis surface 103. In one embodiment, transducer 116 includes an ultrasonic flow measurement system. In one embodiment, transducer 116 includes a laser based Doppler flow measurement system. In one embodiment, transducer 116 includes a catheter based flow measurement system. In one embodiment, transducer 118 includes a load cell or load washer. In one embodiment, transducer 120 includes a displacement measurement system. In one embodiment, transducer 120 includes a strain measurement system. In varying embodiments transducer 120 includes an optical based 2D and 3D measurement system.

In one embodiment, transducer 118 of FIG. 1A is an axial load measuring sensor placed in-line with the bioprosthesis 101 to determine axial stress imparted on the bioprosthesis 101. The axial elongation or displacement of the bioprosthesis 101 is shown in the figure as 121 and is measured using transducer 120.

The system 100 also includes pressure sensors 132, 134, 136, temperature sensor 138, and sensor 140 for determining relative humidity, along with $CO_2$ monitoring system 142 and $O_2$ monitoring system 144 for measuring levels and/or controlling $CO_2$ and $O_2$ levels and/or flow. For convenience, the control and signal connections to and from these sensors and transducers are not shown. Upon reading and understanding the description herein, one skilled in the art will appreciate other measurement systems to be used without departing from the scope of the present system.

Figure 1B:
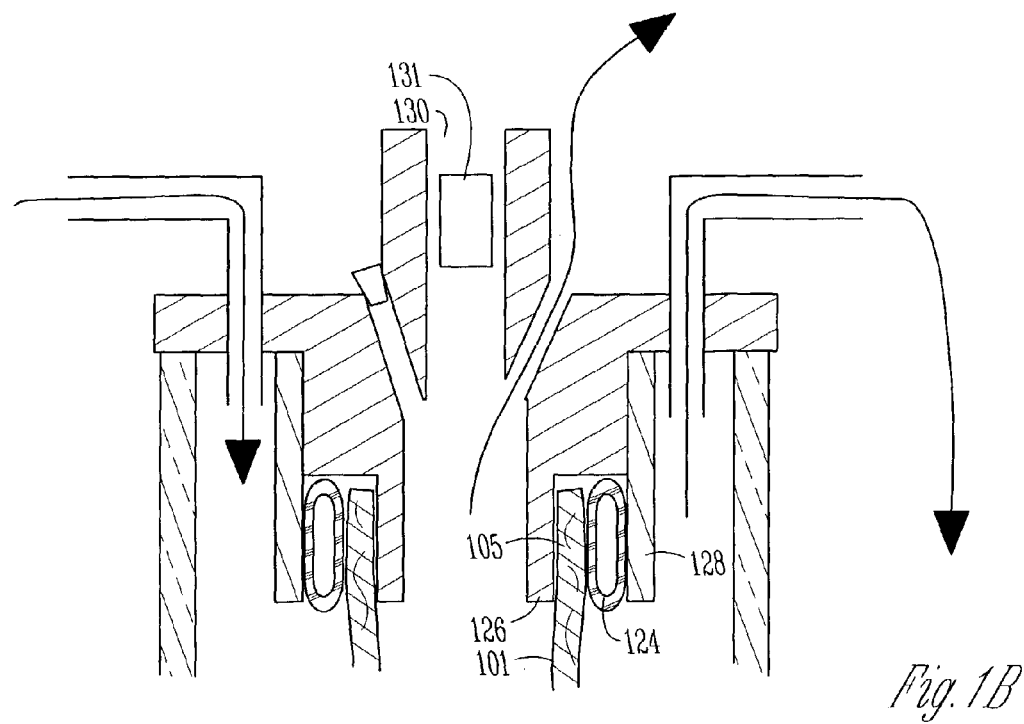
FIG. 1B shows one exemplary embodiment of a soft clamp assembly that can be used in the microprocessor controlled bioreactor of FIG. 1A, according to one embodiment of the present invention.

In this embodiment, soft clamps 122-1, 122-2 hold the bioprosthesis 101 in position. The soft clamps 122-1, 122-2 are intended to provide secure attachment of the bioprosthesis 101 without damaging it. In one embodiment, soft clamps 122-1 and 122-2 are rubber clamps. In one embodiment, as provided by FIG. 1B, the soft clamp 122-1 includes an expandable cuff 124. In one embodiment the expandable cuff 124 is an inflatable cuff that mechanically biases the bioprosthesis end portion 105 against a rigid internal ring 126. The inflatable cuff 124 can exert force, since it is constrained by the rigid external ring 128. In one embodiment, the inflatable cuff 124 is a doughnut shape. In one embodiment, the inflatable cuff 124 is inflated with air. In one embodiment, the inflatable cuff 124 is inflated with fluid. In varying embodiments, the cuff inflation pressure is controllable. One embodiment incorporates fixed volumetric displacement to create and control inflation pressure. Other expandable cuffs are possible without departing from the scope of the present system. In one embodiment, the rigid internal ring 126 is smooth. In one embodiment, the rigid internal ring 126 is textured or ridged to provide better grip on the bioprosthesis end portion 105. In an embodiment, the rigid internal ring 126 and the rigid external ring are metals. Other embodiments and biasing systems are possible without departing from the scope of the present soft clamp approach. In FIG. 1B, the soft clamp for clamp 122-1 is shown on the upper portion of the bioreactor. Such a clamp, a soft clamp for clamp 122-2 may be used on the bottom portion to grip the lower bioprosthesis end portion.

The system 100 of FIG. 1A also shows an access port 130 for additional transducers, or a camera, or for other monitoring or inspection equipment 131. Access port 130 is closed off to provide closed operation of system 100. Port plugs 146 are also used to close extra ports which are not connected to system conduits with fluid flows. The system is shown with arrows to and from pumps 108, 110 and 112 to indicate contained flows to and from the pumps. The arrows indicate fluid flow in a conduit. The closed system keeps fluids contained in the various components and conduits. In one embodiment of system 100, the design includes metal for portions 1-6, glass for portion 7, and plastic for portion 8.

Figure 2:
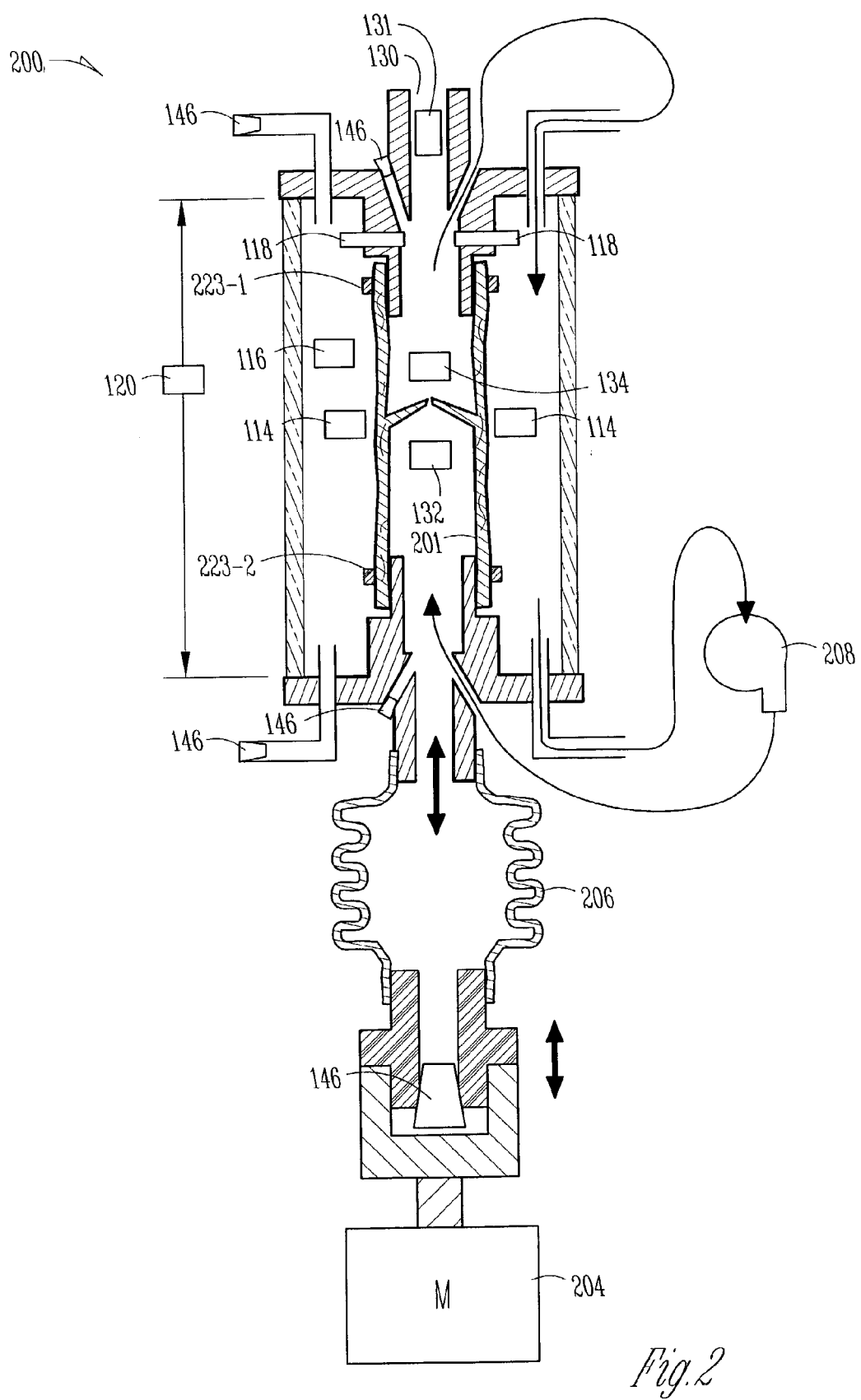
FIG. 2 is one embodiment of a microprocessor controlled bioreactor with a recirculation design according to one embodiment of the present invention.

FIG. 2 provides one embodiment of a servocontrolled bioreactor configuration 200 utilizing a mean flow pump 208 and a recirculating design where fluid pressurably introduced into the central portion of bioprosthesis 201 is transmitted via the right hand ports of the bioreactor before returning to the mean flow pump 208. The linear motor 204 drives the dynamic pump 206. In this embodiment, tie wraps 223-1 and 223-2 keep the bioprosthesis 201 in position. In an embodiment tie wraps 223-1 and 223-2 are plastic. It is understood that a soft clamp as provided in FIG. 1B is employed in alternate embodiments of the system. The sensor and monitoring systems mentioned in connection with FIG. 1A are used in varying embodiments. FIG. 2 shows only some possible transducers for convenience and brevity; however, it is understood that several sensor configurations are possible without departing from the scope of the present system. FIG. 2 also shows plugs 146 used to provide closed system operation.

Figure 3B:
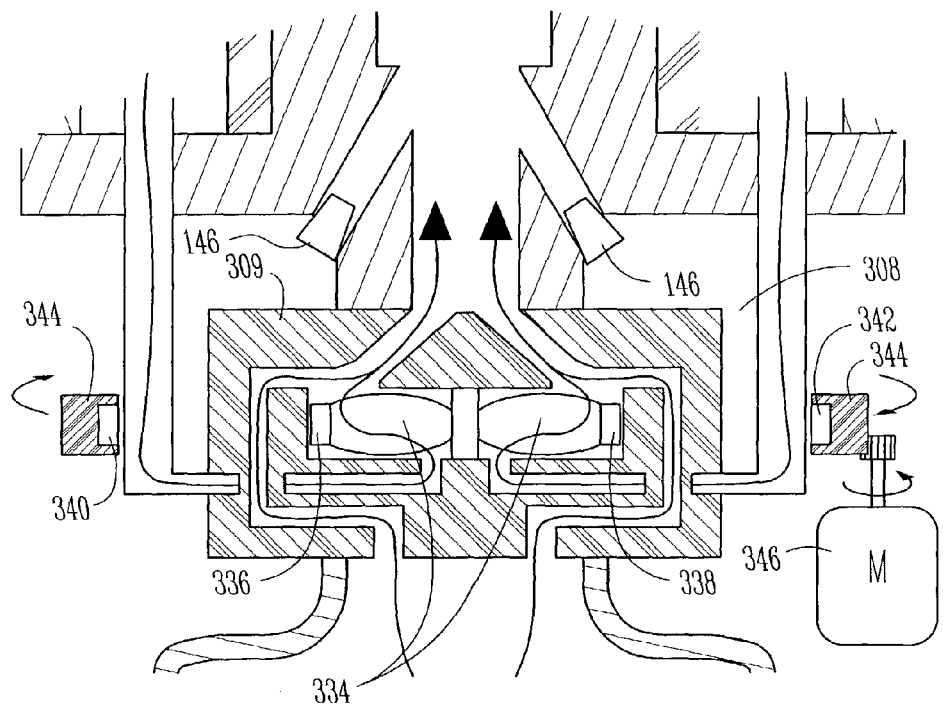
FIG. 3B is a detailed layout of one embodiment of an integrated mean flow pump that can be used in the microprocessor controlled bioreactor of FIG. 3A, according to one embodiment of the present invention.
Figure 3A:
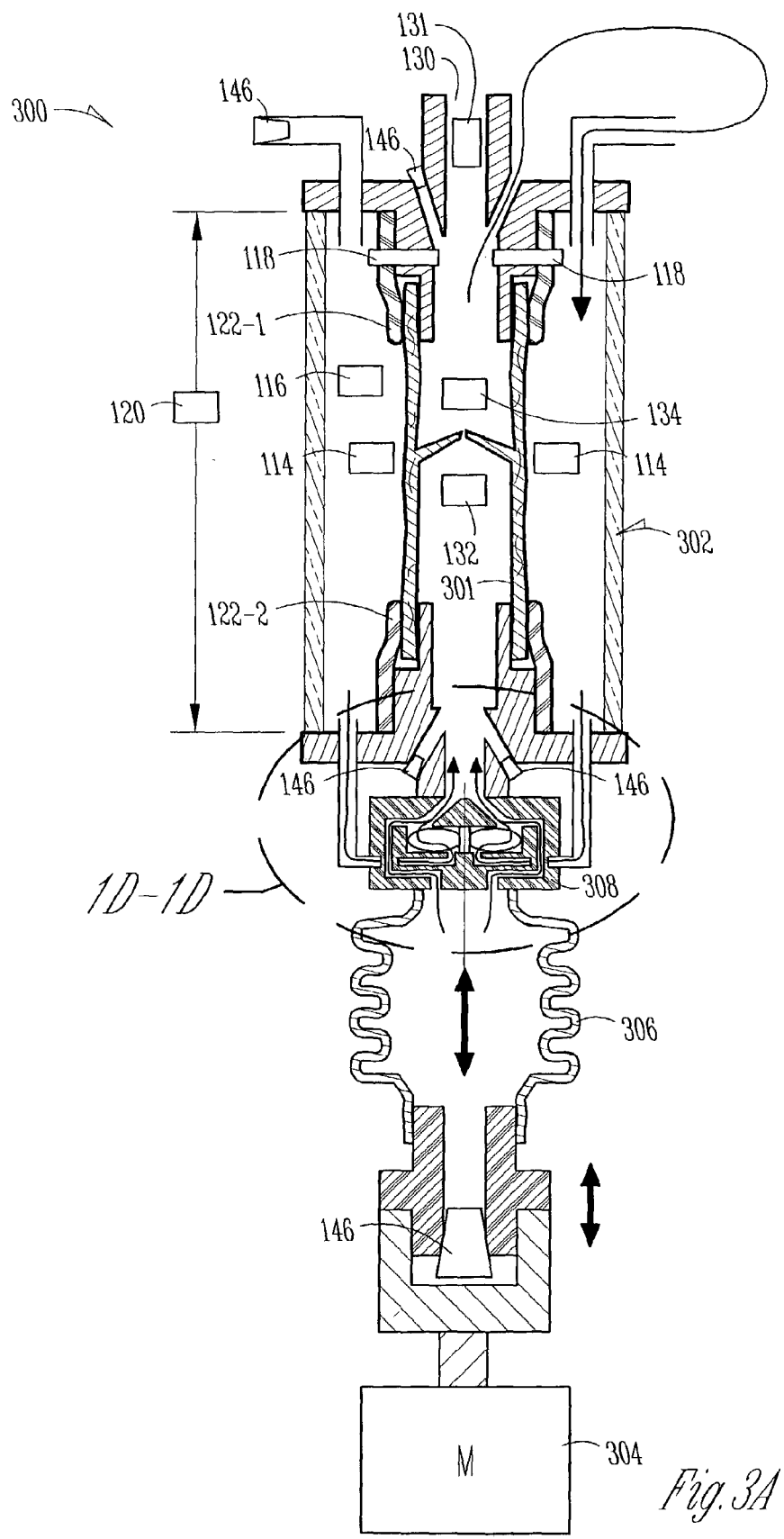
FIG. 3A is one embodiment of a microprocessor controlled bioreactor with self contained pumps according to one embodiment of the present invention.

FIG. 3A provides one embodiment of a servocontrolled bioreactor configuration 300, which includes an integrated mean flow pump 308. In one embodiment, the bioreactor 302 is designed for one use. Such a design may be considered disposable. In one embodiment, the internal volume is kept small to reduce the amount of nutrient fluid required throughout the process. The linear motor 304 drives the dynamic pump 306. The sensor and monitoring systems mentioned in connection with FIG. 1A are used in varying embodiments. FIG. 3A shows only some possible transducers for convenience and brevity; however, it is understood that several sensor configurations are possible without departing from the scope of the present system. In one embodiment, external transducers are employed to reduce the risk of contaminating the bioprosthesis 301. It is understood that soft clamps, as provided in FIG. 1B, are employed in alternate embodiments of the system. A tie wrap system is used in additional embodiments. The integrated mean flow pump 308 of FIG. 3A is demonstrated by an example provided in FIG. 3B.

The integrated mean flow pump 308 of FIG. 3B includes an internal rotary vane 334 in housing 309. In this embodiment, magnets 336, 338 are placed at the tip of each vane. The magnets 336, 338 are magnetically coupled to magnets 340, 342 in a larger ring 344 that fits around the reactor. The ring 344 is mounted on bearings and rotates about the centerline of the reactor by means of rotary motor 346. In one example, the rotary motor 346 is a DC motor. The speed of the motor 346 is controlled by a computer. In one embodiment, the integrated mean flow pump 308 is a gear type pump. In one embodiment, the housing 309 for integrated mean flow pump 308 is plastic. In an embodiment, internal rotary vane 334 is a fan blade. Upon reading and understanding the present teachings it is possible that one skilled in the art could identify self-contained designs that do not depart from the scope of the present system.

Figure 4:
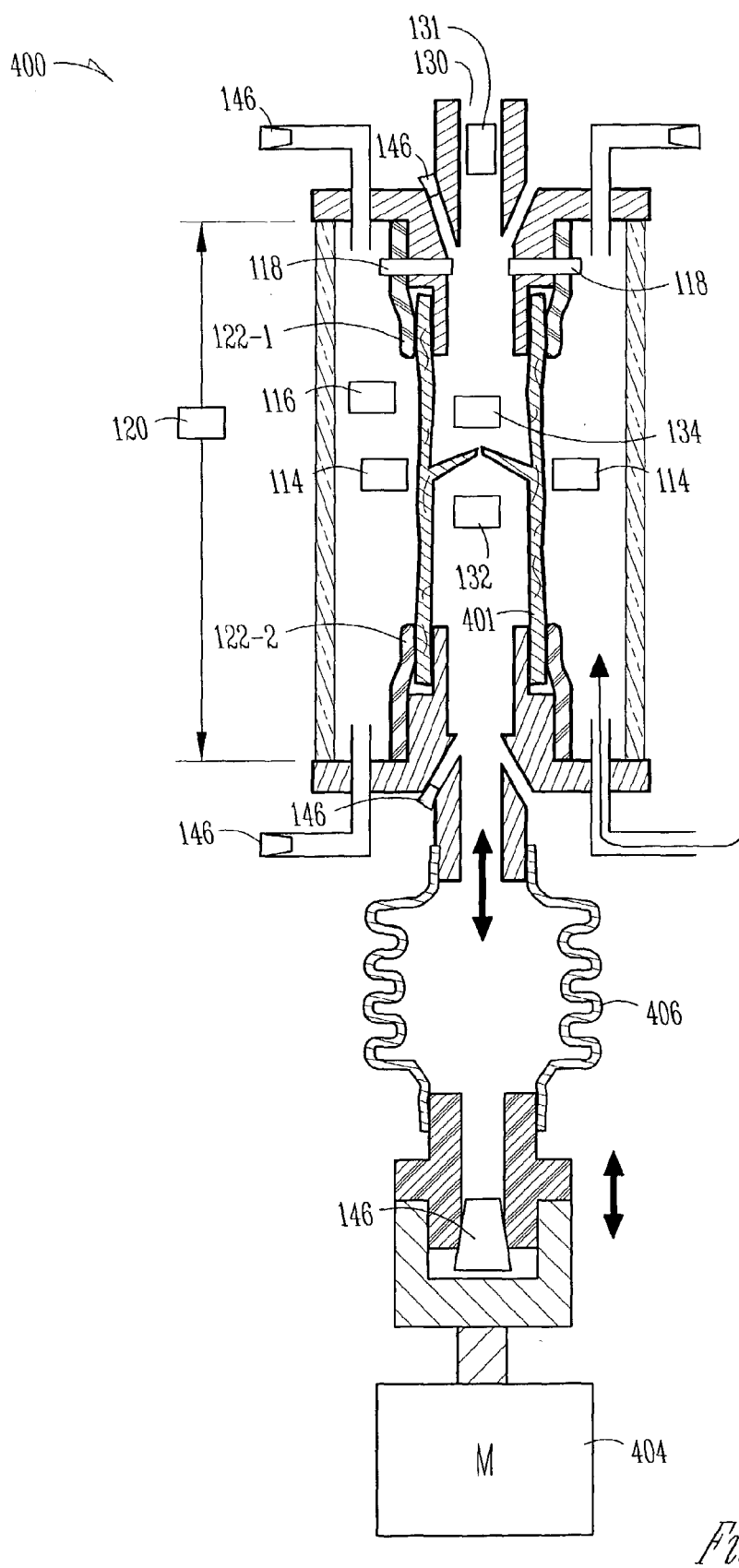
FIG. 4 shows one example of a bioreactor with dynamic alternating flow according to one embodiment of the present invention.

Different applications may call for different flow patterns and bioreactor configurations. FIG. 4 provides an example of a bioreactor 400 with a dynamic pump 406 only. Such a design is useful for, among other things, creation of high pressure differentials for the conditioning of other bioprostheses 401, such as inner ear prostheses. The linear motor 404 drives the dynamic pump 406. It is understood that soft clamps, as provided in FIG. 1B, are employed in alternate embodiments of the system. A tie wrap system is used in additional embodiments. The sensor and monitoring mentioned in connection with FIG. 1A, are used in varying embodiments and only some of the possible sensors are shown. Other sensor configurations may be used without departing from the teachings of the present application.

Figure 5:
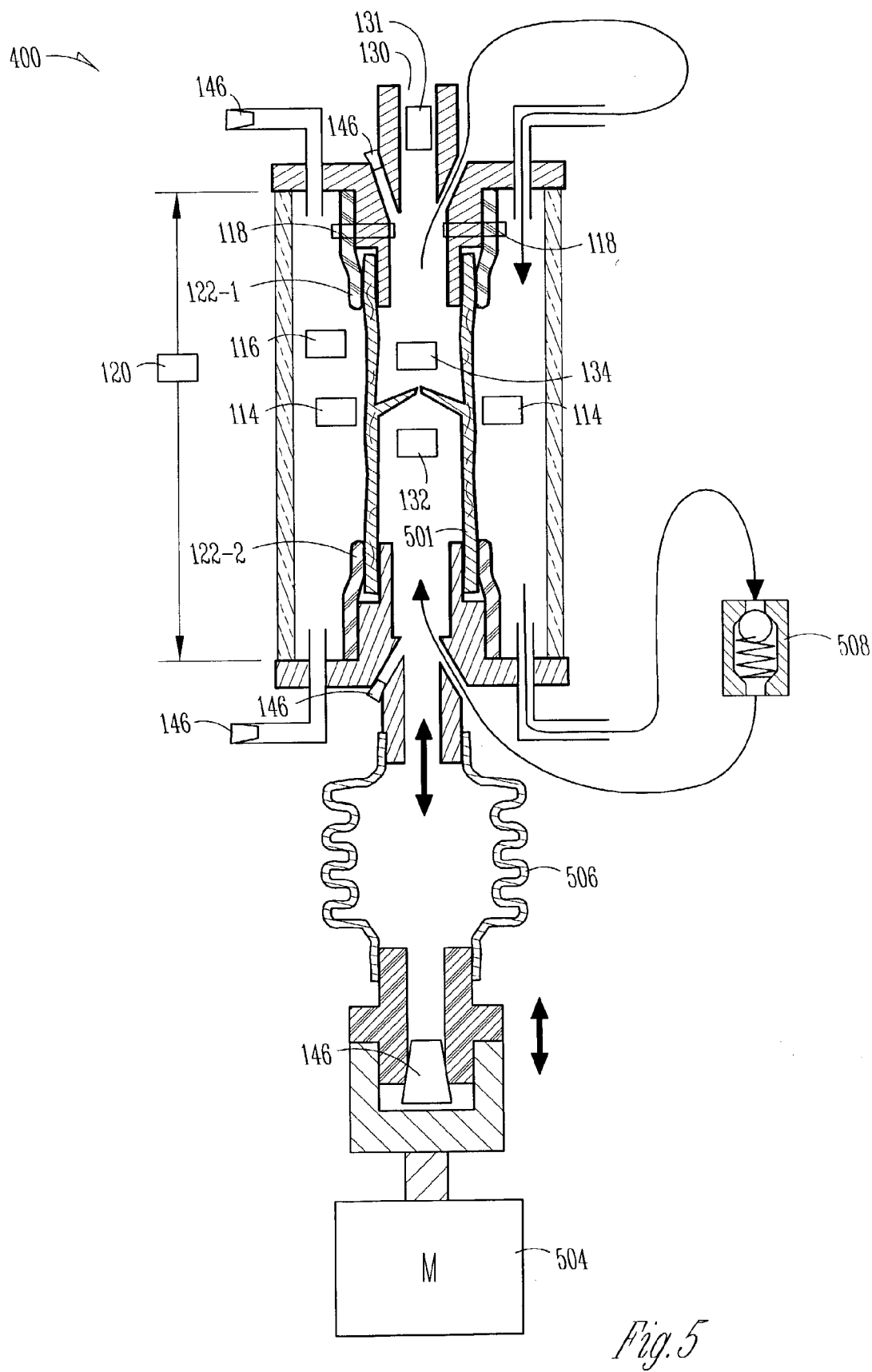
FIG. 5 shows one example of a bioreactor with dynamic alternating flow with a checkvalve according to one embodiment of the present invention.

Another bioreactor configuration 500 incorporating a dynamic pump 506 and a checkvalve 508 is provided in FIG. 5. In this embodiment, the checkvalve 508 can be used to make a valved bioprosthesis 501 work harder once it reaches a critical development stage. Such a design is useful for conditioning heart valve and venous bioprostheses. In one embodiment, the checkvalve 508 is a flapper valve.

In one embodiment, checkvalve 508 is a ball valve. Other valves may be used. In one embodiment, two bioprosthesis valves could be used. Other one way valves are incorporated in alternate embodiments, and the configuration may vary without departing from the scope of the present system. The linear motor 504 drives the dynamic pump 506. It is understood that a soft clamps, as provided in FIG. 1B, are employed in alternate embodiments of the system. A tie wrap system is used in additional embodiments. The sensor and monitoring systems mentioned in connection with FIG. 1A, are used in varying embodiments and only some of the possible sensors are shown. Other sensor configurations may be used without departing from the teachings of the present application.

Figure 6:
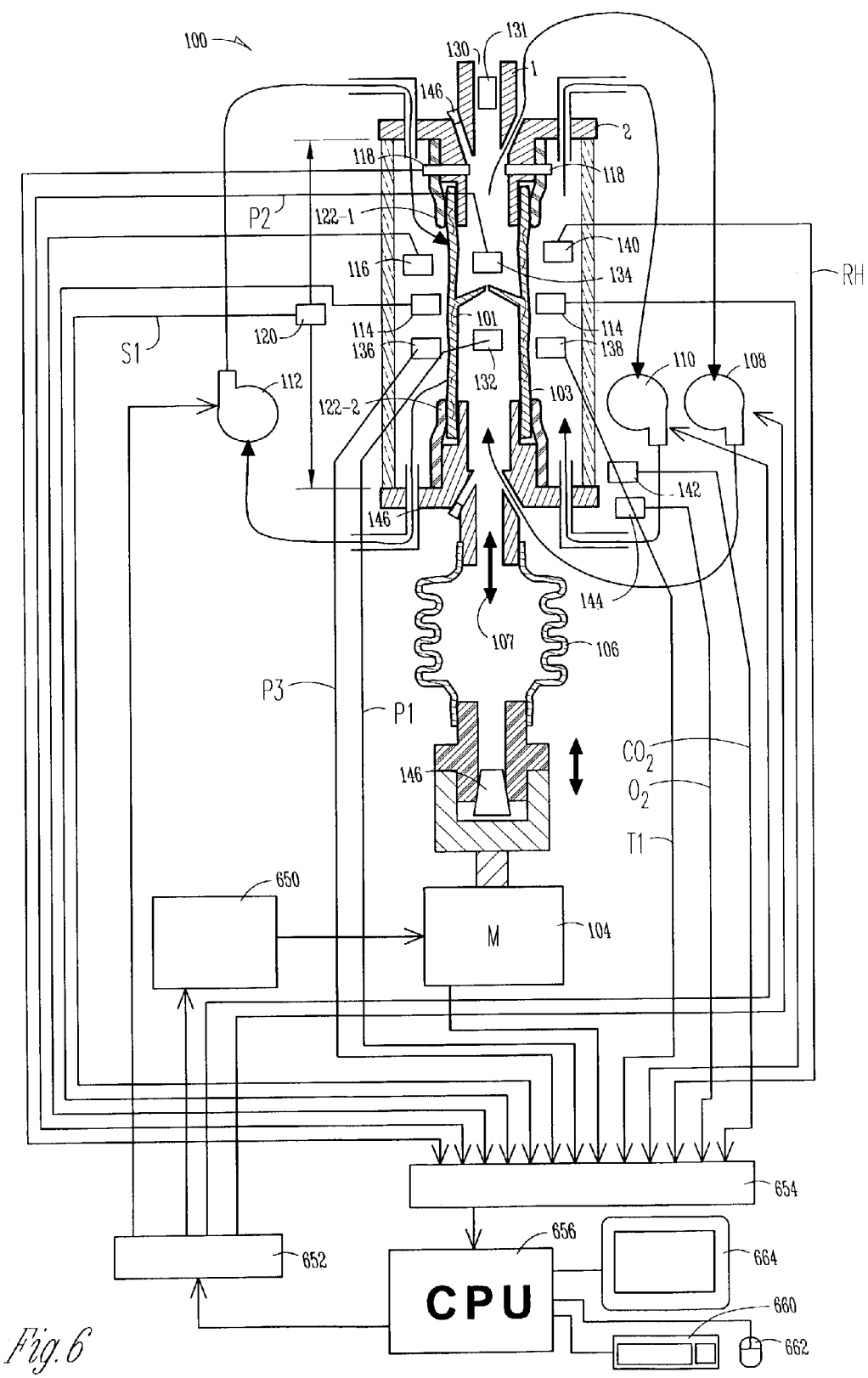
FIG. 6 is a functional diagram of a bioreactor system according to one embodiment of the present invention.

FIG. 6 is a functional diagram showing signals between exemplary bioreactor 100 of FIG. 1A, linear motor amplifier 650, output conditioner 652 and input conditioners 654, and the central processing unit (CPU) 656. Signals from various transducers including 114, 116, 118, and 120 are processed and provided to the CPU 656 via input conditioners. Signals from pressure sensors 132, 134, and 136 denoted as P1, P2, and P3, respectively, a signal denoted as SI representing the "stretch" 121, a signal denoted as T1 from temperature sensor 138, a signal denoted as RH from the relative humidity sensor 140, and signals denoted as CO2 from $CO_2$ monitoring system 142 and $O_2$ from $O_2$ monitoring system 144 representing oxygen and carbon dioxide levels and/or flow are also sent to the CPU 656 via input conditioners 652. The linear motor signal is also supplied to the CPU 656 via input conditioners 656.

Output signals are provided to the mean flow pumps 108, 110, and 112 and to the motor amplifier 650. It is understood that signals may be transmitted to the transducers 114 and 116 as needed to implement the desired signal sensing. It is also understood that in varying embodiments conditioning means may be used for each transducer for proper signal generation.

The CPU 656 couples to a user environment via a user interface. The user interface may include a keyboard 660, a mouse 662 or other select device, and a monitor 664.

In varying embodiments the CPU 656 is capable of controlling several operations, including, but not limited to:

Dynamic Pump Control: The CPU 656 monitors the linear motor position (dynamic pump displacement) using an LVDT or other transducer that is connected to the motor 104. It uses this signal as the feedback in a digital PID loop. The output signal from the PID loop drives the linear motor amplifier 650, which in term drives the motor 104. The CPU 656 also creates an input waveform for the PID loop. This waveform can be any shape and it is created by the user using simple segments (sines, ramps, square or other waveform) or discrete points.

Mean Flow Pump(s) Control: In another control loop(s), the CPU 656 monitors flow conditions and adjusts the flow rate produced by the mean flow pump. The flow rate feedback includes, but is not limited to, a signal from a flow transducer or the pump volumetric output (assumes calibrated pump with speed output).

Environment Monitoring and Control: The CPU 656 monitors the $CO_2$, $O_2$, RH (relative humidity) and temperature levels. These parameters can be controlled by placing the entire bioreactor 100 into an incubator, by routing pre-conditioned air from an incubator into the bioreactor 100, by adding $CO_2$ or $O_2$ injection and heating into the flow loop, or by adding preconditioned nutrients into the loop.

Data Acquisition of all Transducers: The CPU 656 provides data acquisition for all sensors. To avoid any acquisition aliasing the acquisition rate is generally in the 2 to 8 kHz range. Other acquisition ranges are possible without departing from the scope of the present system.

Checking for Out of Tolerance Conditions: The CPU 656 checks all of the transducer readings to ensure that they are within certain desired conditions. For example, if the differential pressure (P1-P2) drops dramatically, this might indicate that there is a tear in the bioprosthesis 101. Alternatively, if the PID loop error increases substantially, this might indicate that the bioprosthesis 101 is plugged.

Figure 7A:
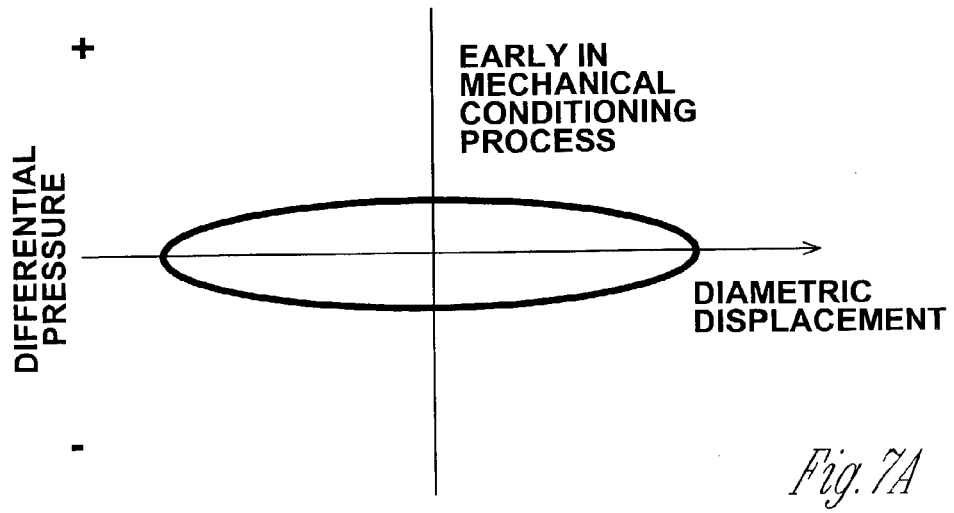
FIG. 7A shows a plot demonstrating one example of diametric displacement versus differential pressure for a specimen early in a mechanical conditioning process of an embodiment.
Figure 7B:
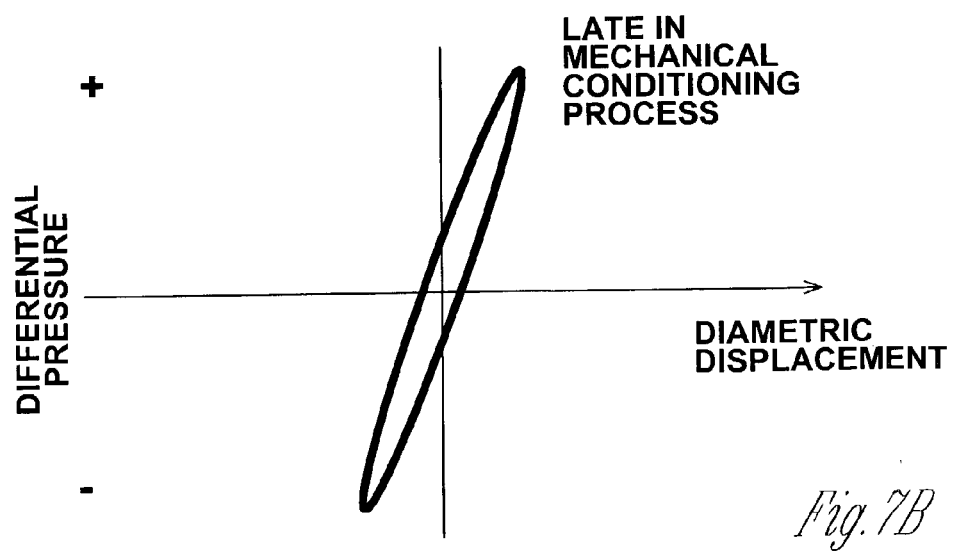
FIG. 7B shows a plot demonstrating one example of diametric displacement versus differential pressure for a specimen late in a mechanical conditioning process of an embodiment.

Analysis of Bioprosthesis Response and Material Properties: FIGS. 7A and 7B shows what the response of the bioprosthesis 101 might look like in the early and later stages of conditioning.

In the early stages as shown in FIG. 7A, the specimen is very compliant and the applied dynamic flow causes large diametric displacement with little applied differential pressure between the inside and outside of the prostheses. The biomaterial also behaves very viscous and shows much damping.

In the later stages as shown in FIG. 7B, the bioprosthesis 101 exhibits a "tighter" response. The applied dynamic flow creates a higher differential pressure with less diametric displacement. The loop is also more closed indicating that the biomaterial is behaving more elastically.

The same kind of response may also be performed using the axial, torsion, or bend load and displacement transducer measurements. Using a Fast Fourier Transform (FFT), the pressure/displacement response can be separated into the real (elastic) and imaginary (viscous) response components. These key components can be used to determine how well the bioprosthesis 101 is responding to the mechanical conditioning process. In alternate embodiments other methods and systems are used to measure the response, including, but not limited to, Neural Networks and systems involving timed domain measurements.

Graphical Interface and User Input: The CPU 656 provides all of the transducer information in a graphical format making it easy for an operator to see what is happening with the process. The transducer waveforms and control signals can all be plotted with respect to time or one another. The instantaneous transducer readings also can be viewed. The interface also enables the user to set up the conditioning waveform and other parameters. These settings can be used for conditioning subsequent bioprostheses.

Logical Sequencing or Intelligent Adaptation: The user is able to program the CPU 656 to make decisions about the proper conditioning sequence or "recipe" to use based on the bioprosthesis response. It is expected that the CPU 656 can also be programmed to adapt the conditioning sequence to provide the optimum cell growth rate or strength. This enables the bioreactor 100 to grow the bioprosthesis 101 from start to finish with little or no operator supervision.

Figure 8A:
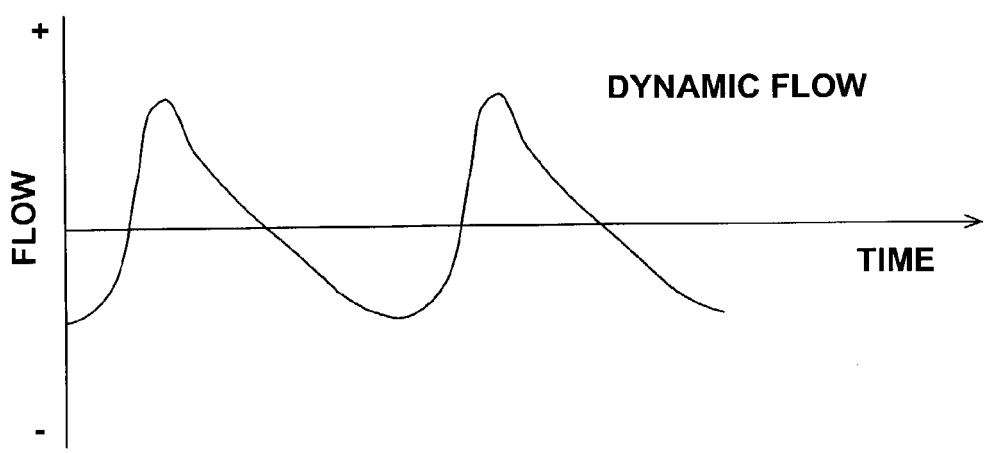
FIGS. 8A, 8B, and 8C are a series of graphs demonstrating dynamic flow, mean flow, and combined dynamic and mean flow with respect to a dynamic pump and mean pump of one embodiment.
Figure 8B:
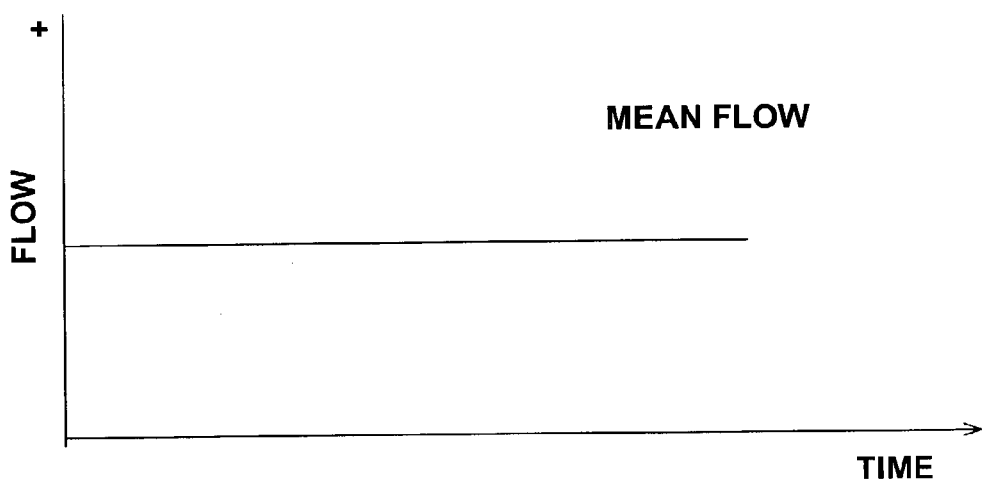
Figure 8C:
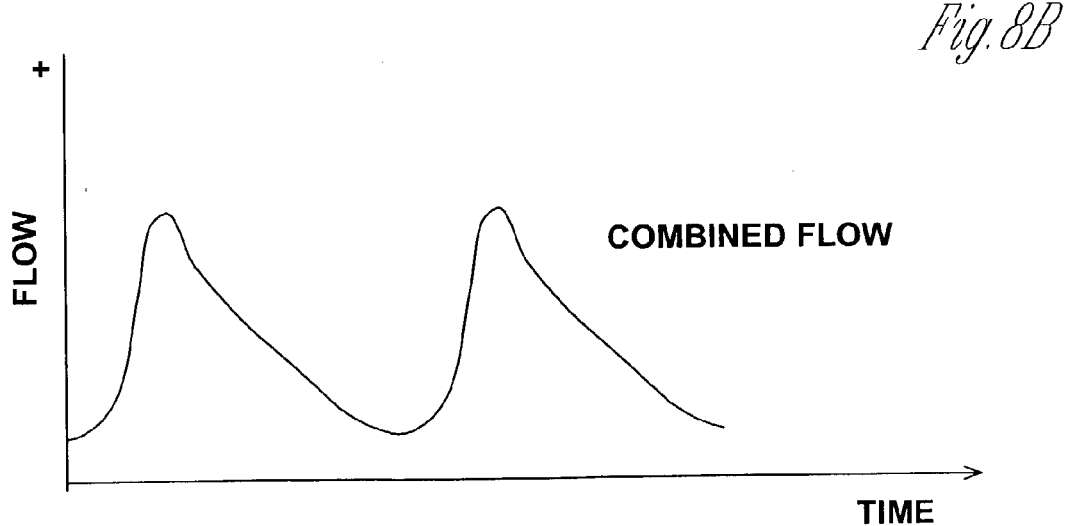

FIGS. 8A, 8b, and 8C are a series of graphs demonstrating dynamic flow, mean flow, and combined dynamic and mean flow with respect to a dynamic pump 106 and mean pump 108, 110, and/or 112 from FIG. 1A in one embodiment. These figures show how the dynamic pump 106 and mean pump 108, 110, and/or 112 work together to provide physiologic flow. Although the dynamic pump 106 can be programmed to create almost any dynamic flow profile, the average of the output must be zero. The mean flow pump 108, 110, and/or 112 offsets the dynamic pump's output to create a flow that is more physiologic-like (flow greater than zero). The combination of the two flows can be used to create flow profiles that are either physiologic, sub-physiologic or super-physiologic. This provides many possibilities for conditioning the vascular bioprosthesis 101.

FIGS. 9A, 9B, 9C, and 9D show different views of a tissue valve conditioner in a general embodiment of the present invention. These views illustrate the general structure for an embodiment including a bioreactor chamber 902, motor 904, dynamic pump 906, and mean flow pump 908. Each of these elements can be configured as described in the various embodiments discussed herein.

Figure 9G:
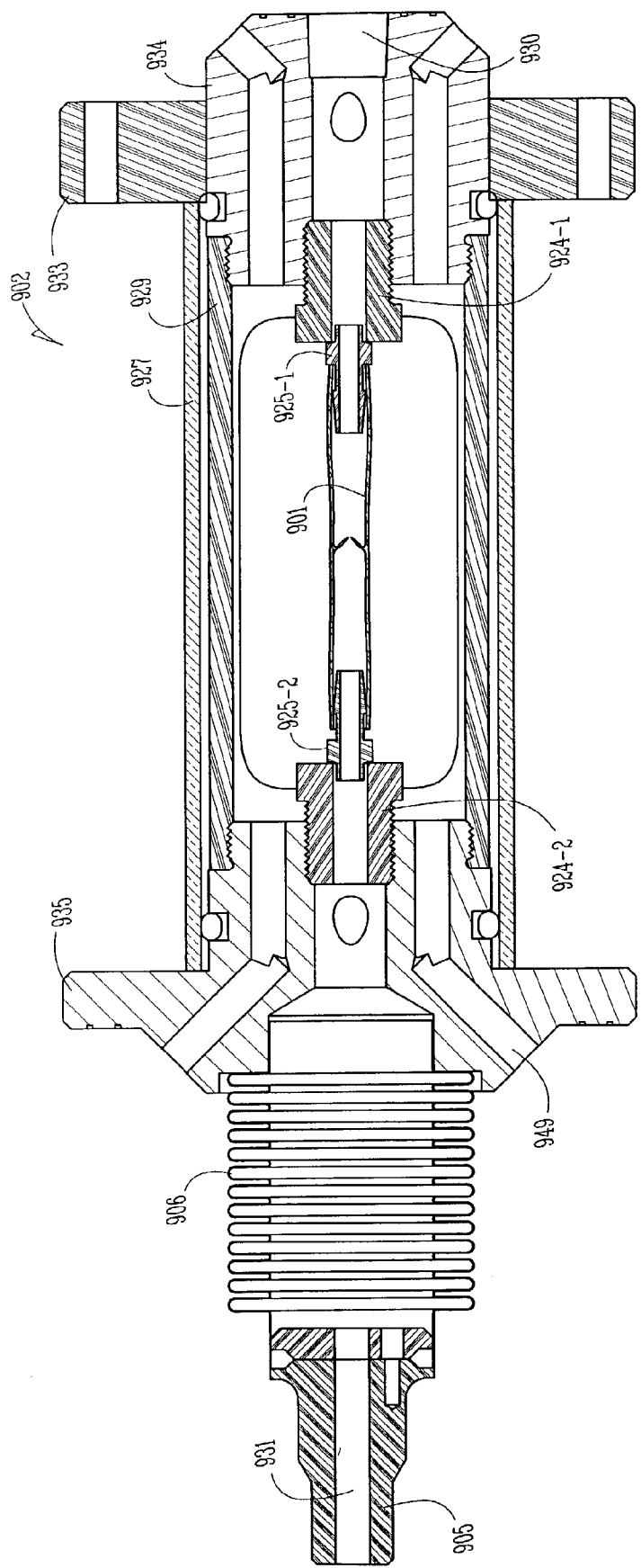

FIGS. 9E, 9F, 9G, and 9H show different views of a bioreactor chamber of the tissue valve conditioner of FIGS. 9A-9D for an embodiment of the present invention. FIG. 9E shows bioreactor chamber 902 coupled to dynamic pump 906. In an embodiment, bioreactor chamber 902 includes a metal cylinder having an opening through it with a glass tube over the metal cylinder, which configuration provides for measuring properties and viewing of a bioprosthesis mounted in the bioreactor chamber 902. In an embodiment, dynamic pump 906 is a bellows pump. FIG. 9F shows a top view looking down on an upper access port 930.

FIG. 9G shows an internal view of bioreactor chamber 902 coupled to dynamic pump 906. In one embodiment, dynamic pump 906 is a metal bellows. Bioreactor chamber 902 includes a glass tube 927 over an internal frame 929. In an embodiment, internal frame 929 is plastic. In another embodiment, internal frame 929 is metal. This configuration provides an upper access port 930 and a lower access port 931. In one embodiment, upper access port 930 is metal and lower access port 931 is plastic. The glass tube 927 is held between an upper tumbling wheel 933 and a lower tumbling wheel manifold 935. In an embodiment, the upper tumbling wheel 933 is plastic and the lower tumbling wheel manifold 935 is metal. Bioreactor chamber 902 is also provided with an external flow port 949. A bioprosthesis 901 is held with attachment fittings 925-1, 925-2. In an embodiment, bioprosthesis 901 can be human tissue or vein. In an embodiment, attachment fittings 925-1, 925-2 are plastic fittings.

Figure 9H:
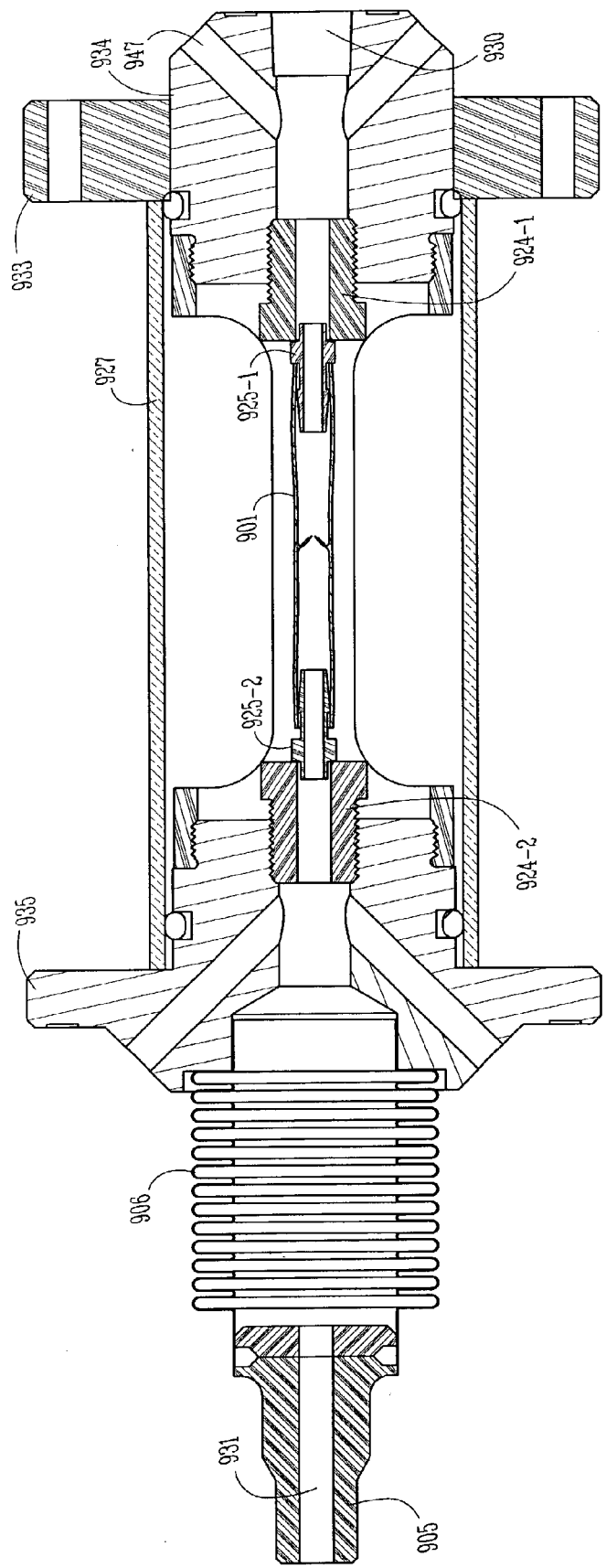

FIG. 9H shows another internal view of the embodiment of bioreactor chamber 902 coupled to dynamic pump 906. Bioreactor chamber 902 includes a glass tube 927. This configuration also provides an internal flow port 947. Bioprosthesis 901 is held with attachment fittings 925-1, 925-2. In an embodiment, bioprosthesis 901 can be human tissue or vein. In an embodiment, attachment fittings 925-1, 925-2 are plastic fittings. In an embodiment, attachment fittings 9251, 925-2 are plastic barb fittings. Attachment fittings 925-1, 925-2 connect to bushings 924-1 and 924-2. In an embodiment, bushings 924-1 and 924-2 are plastic bushings.

Figure 9I:
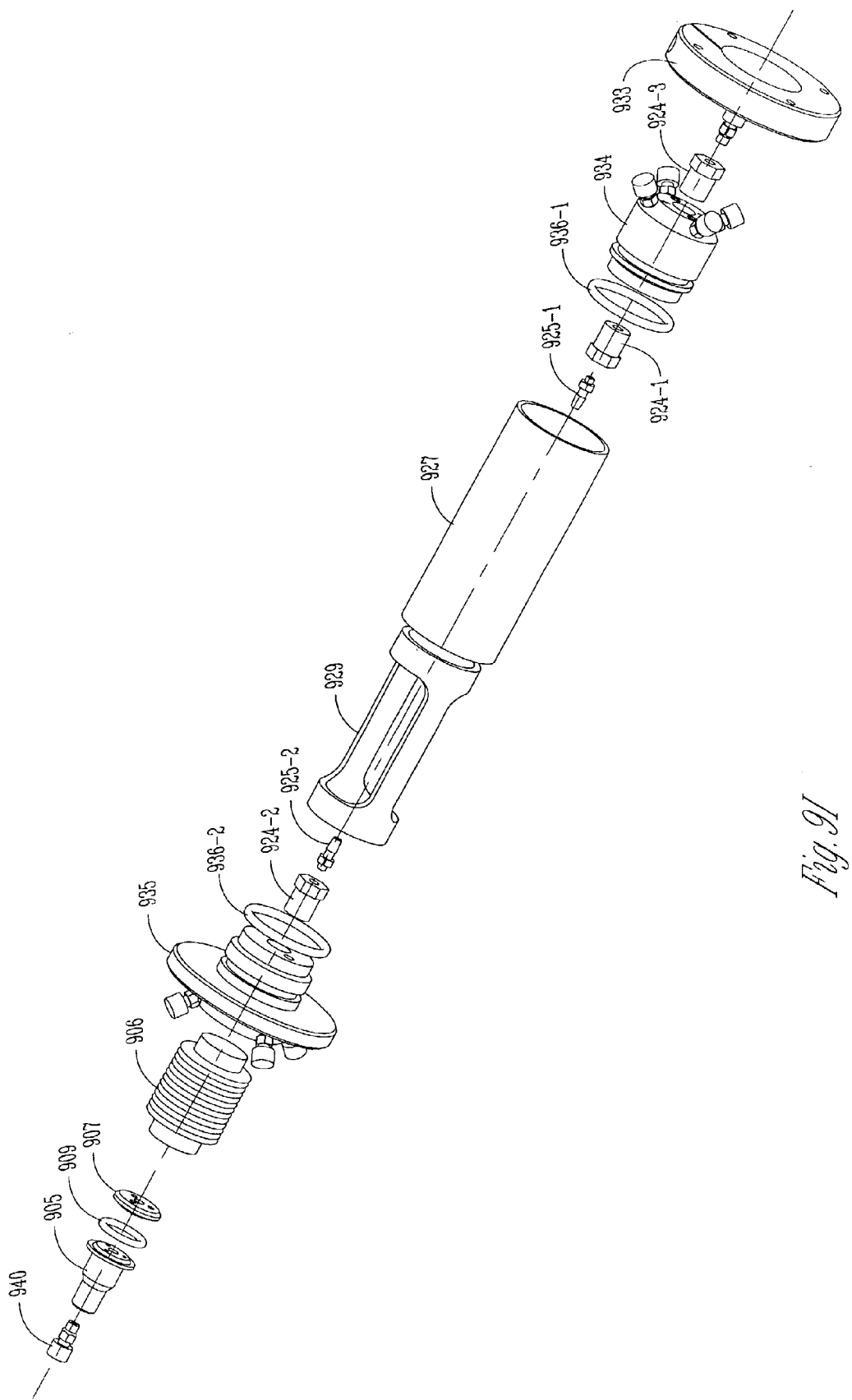
FIG. 9I shows an exploded view of one embodiment of a tissue valve conditioner chamber assembly, according to one embodiment of the present invention.

FIG. 9I shows an exploded view of one embodiment of a tissue valve conditioner chamber assembly. This embodiment of a tissue valve conditioner chamber assembly includes a chamber tube 927 over a chamber standoff 929 mounted to a lower tumbling wheel manifold 935 and top manifold 934 via threaded attachments. Sealing of the tube against the lower tumbling wheel manifold 935 is provided by an o-ring 936-2. Threaded into the lower tumbling wheel manifold 935 is a bushing 924-2 to which is mounted barbed fitting 925-2. The lower tumbling wheel manifold 935 mounts to bellows 906, which is connected to a bellows end 905 by a bellows retaining cap 907 and expansion o-ring 909. Fitting 940 threads into bellows end 905 and provides access for initial seeding of the bioprosthesis. The end of chamber tube 927 is sealed against the top manifold 934 by an o-ring 936-1. Threaded into the top manifold 934 is a bushing 924-1 to which is mounted barbed fitting 925-1. The upper tumbling wheel 933 slides over the top manifold 934 and is clamped in place fixing the chamber tube in place. A bushing 924-3 is threaded into the end of the top manifold 934 and provides access for various transducers or inspection systems.

The configurations presented herein are intended to be demonstrative of the present system, and are not intended in an exhaustive or exclusive sense. Minor variations in components and layout may exist within the scope of the present teachings.

Operation

Figure 10A:
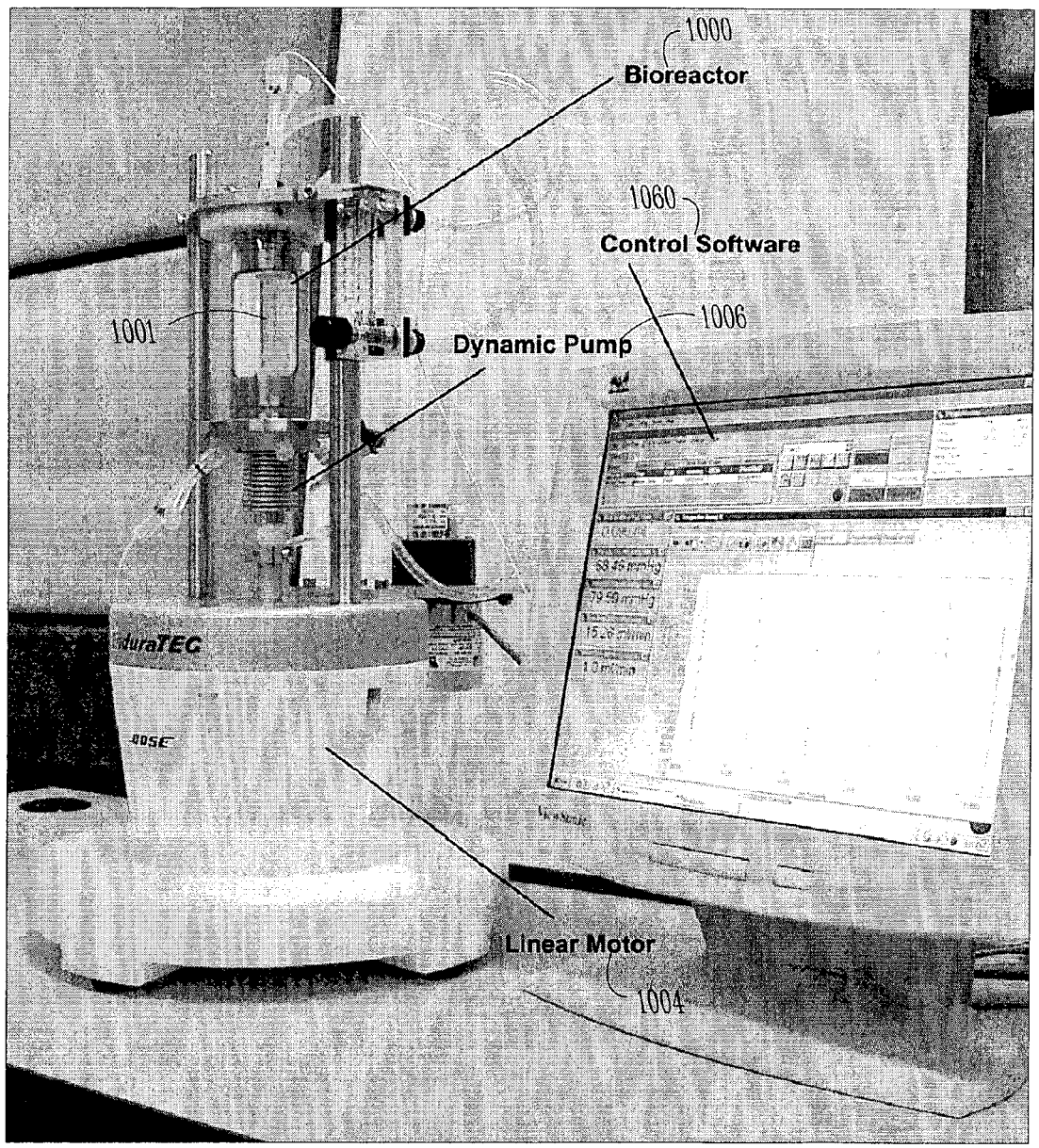
FIGS. 10A, 10C, 10D, 10E, 10F, 10G, and 10H show different views of one embodiment of a microprocessor controlled bioreactor according to one embodiment of the present invention.
Figure 10B:
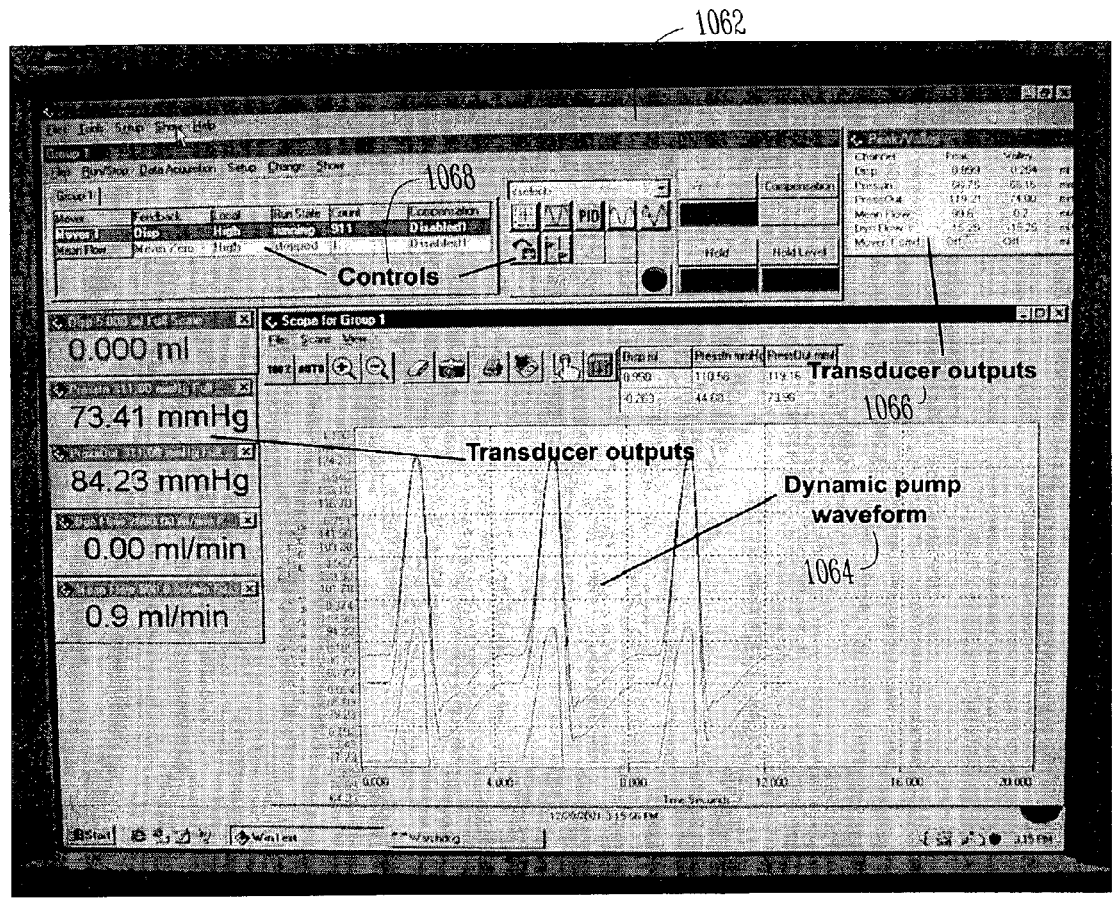
FIG. 10B shows one embodiment of a control software screen according to one embodiment of the present invention.

FIGS. 10A, 10C, 10D, 10E, 10F, 10G, and 10H show different views of one embodiment of a microprocessor controlled bioreactor, while FIG. 10B shows one embodiment of a control software screen.

Figure 10C:
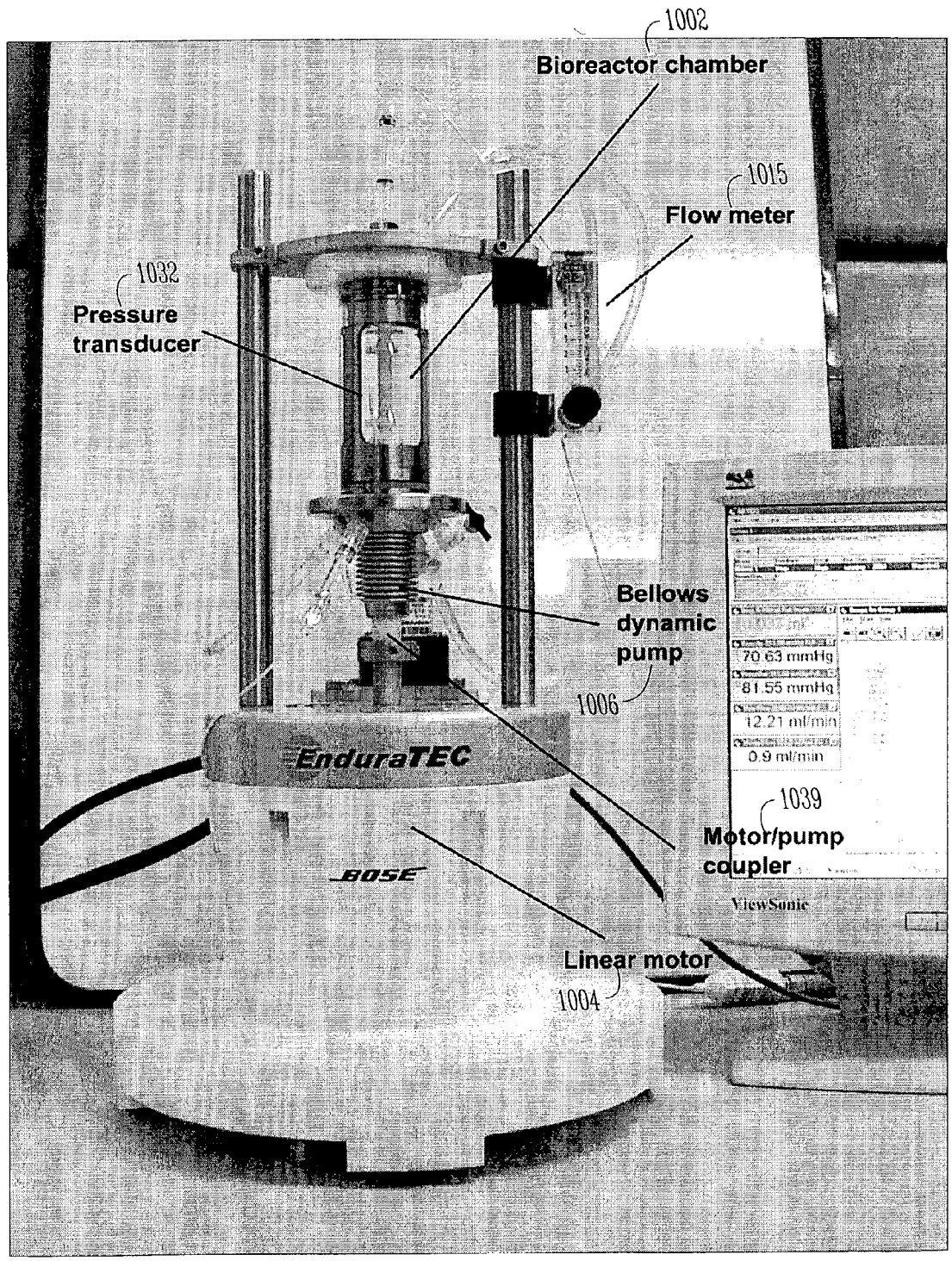
Figure 10D:
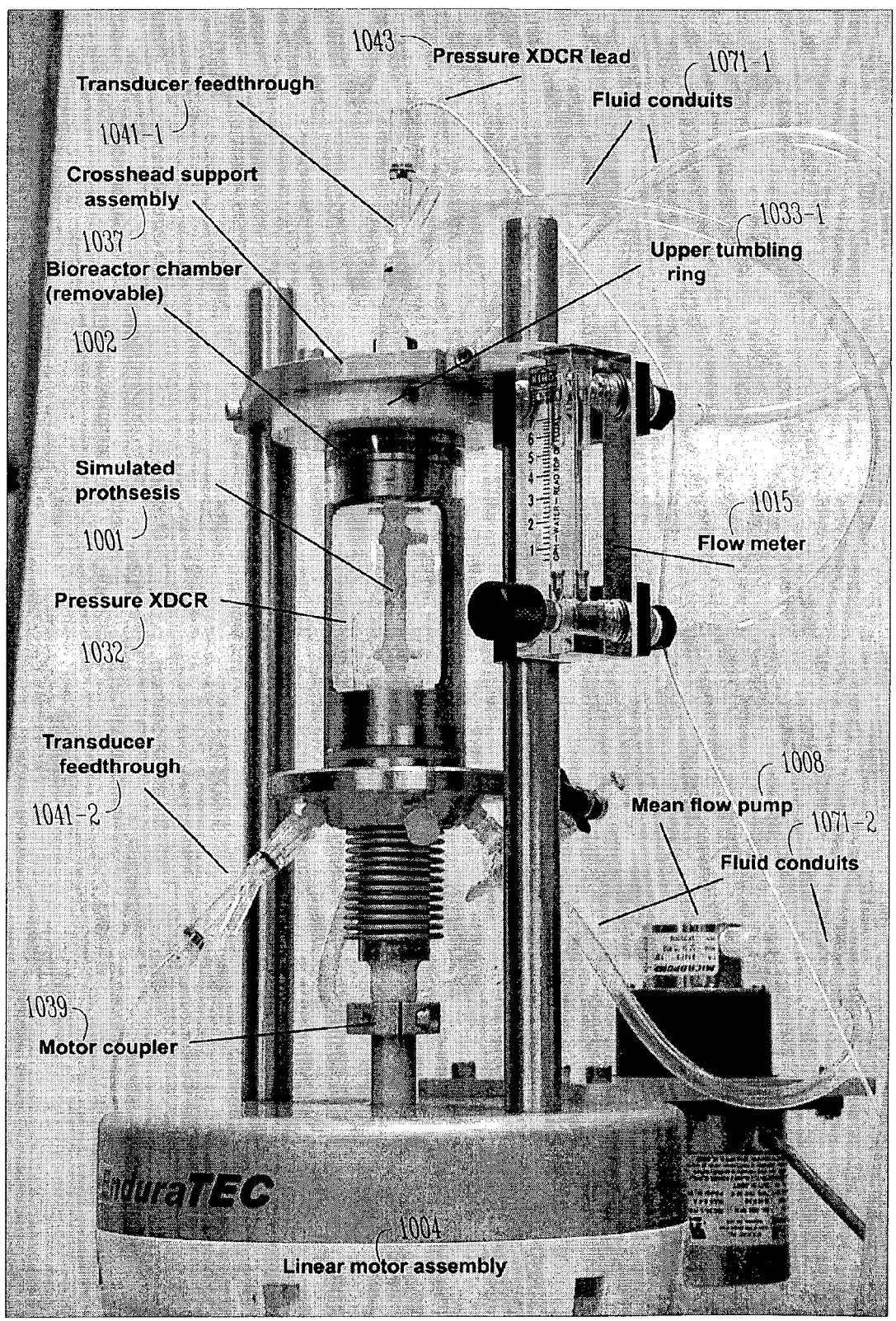

FIGS. 10A, 10C, and 10D show a bioreactor 1000 including a bioprosthesis 1001 and linear motor in a motorized frame for driving the dynamic pump 1006. The control software 1060 on the computer is connected to the linear motor 1004 and transducers to control the motorized frame, which provides the pumping action for the bioprosthesis 1001. FIG. 10B shows one example of a control software screen 1062 including transducer output waveforms, dynamic pump waveforms 1064, transducer outputs 1066, and controls 1068. In one embodiment a graphical user interface is employed to control the system, however, it is understood that alternate embodiments may include different software controls without departing from the present system.

Figure 10E:
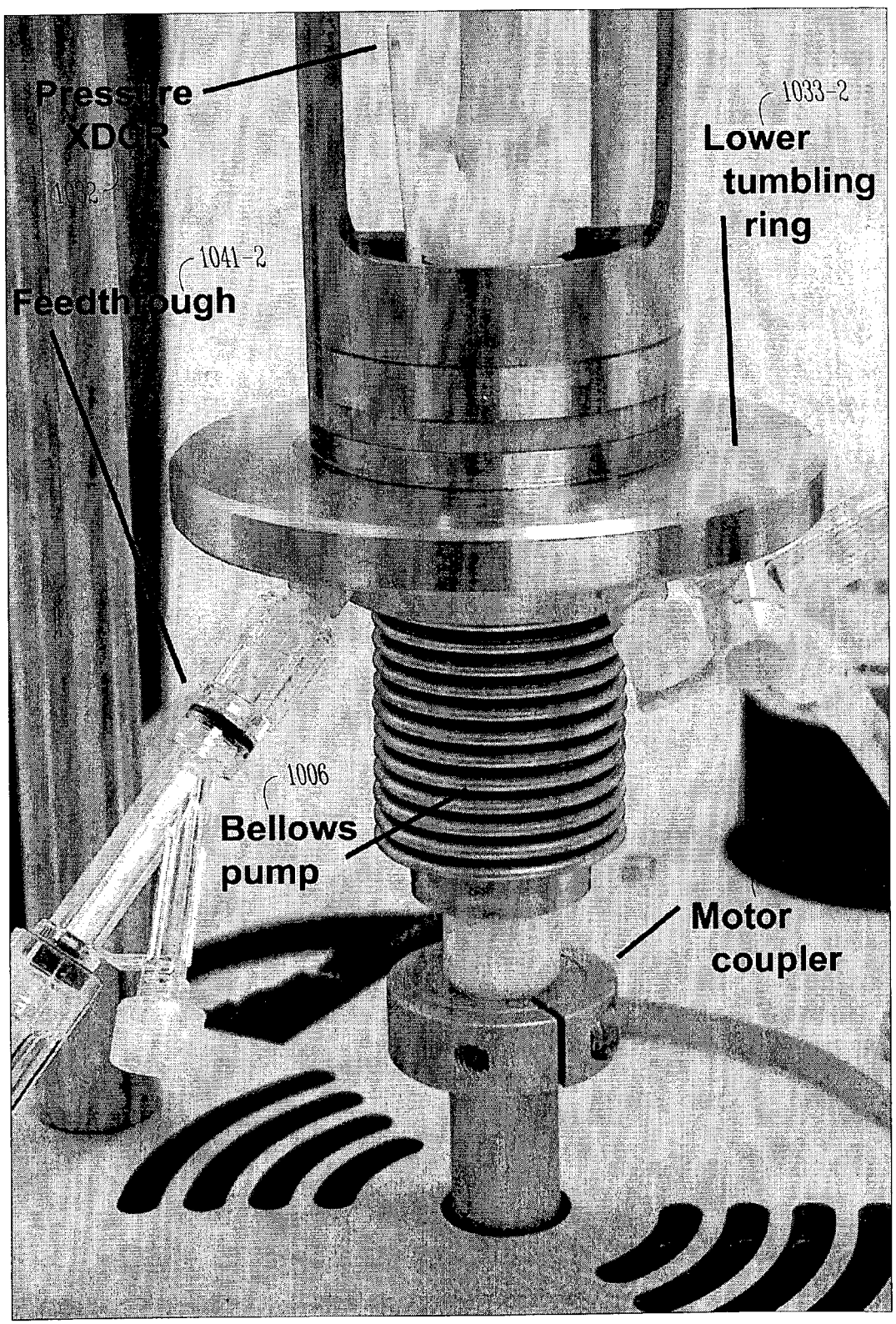

The internal main nutrient fluid flow, Q1, in one embodiment equivalent to flow from mean flow pump 208 of FIG. 2, is controllable over a range from zero to several times physiological flow. The flow is comprised of two components: The mean or steady state flow which is generated by a mean flow pump 1008 (FIG. 10D) and the dynamic flow which is generated by a linear motor driven bellows pump 1006 (FIGS. 10A, 10C, and 10E). In one embodiment, a flow meter 1015 (FIGS. 10C and 10D) is provided for visual reference of the applied mean flow. Use of a linear drive motor 1004 (FIGS. 10A, 10C and 10D) for the dynamic pump increases the number of cycles per minute to which the bioprosthesis 1001 may be subjected. A microprocessor-based controller operates the pulse generation system with varying frequencies (0 to over 6000 cycles/minute) and wave shapes under closed loop control. The dynamic flow waveform can be configured to provide almost any wave shape using the software (screen shown in FIG. 10B). The microprocessor-based controller may be servo controlled, utilizing feedback from a compliance transducer system, linear displacement transducer, and/or pressure transducer.

Figure 10F:
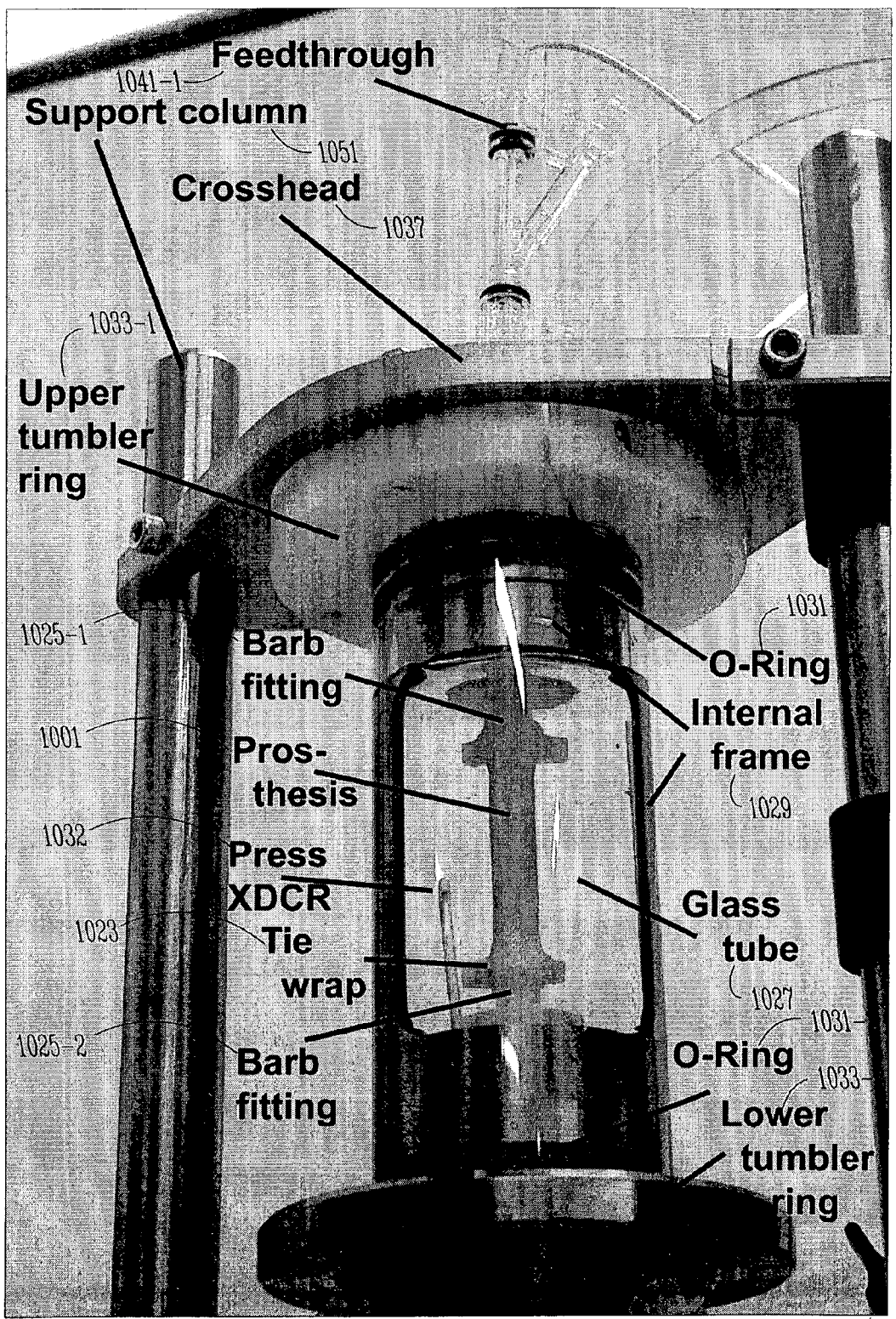
Figure 10G:
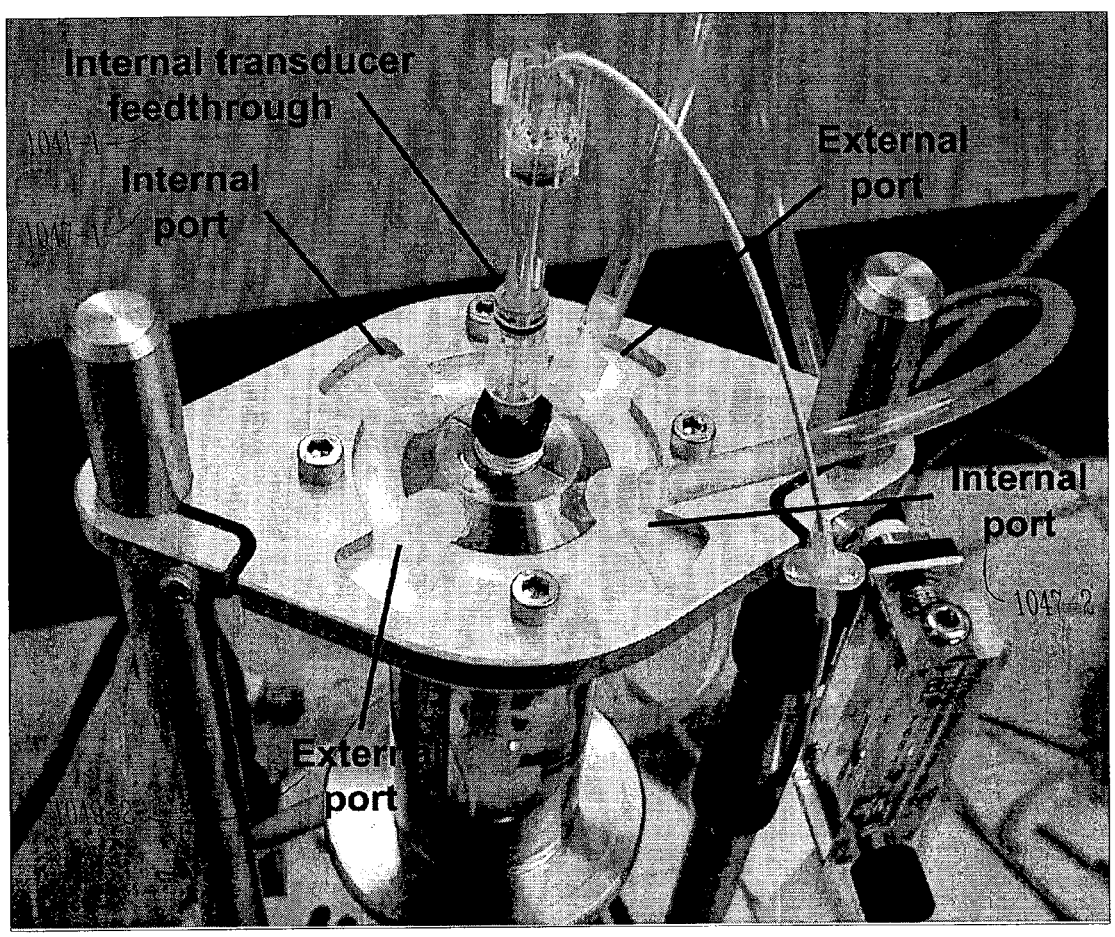
Figure 10H:
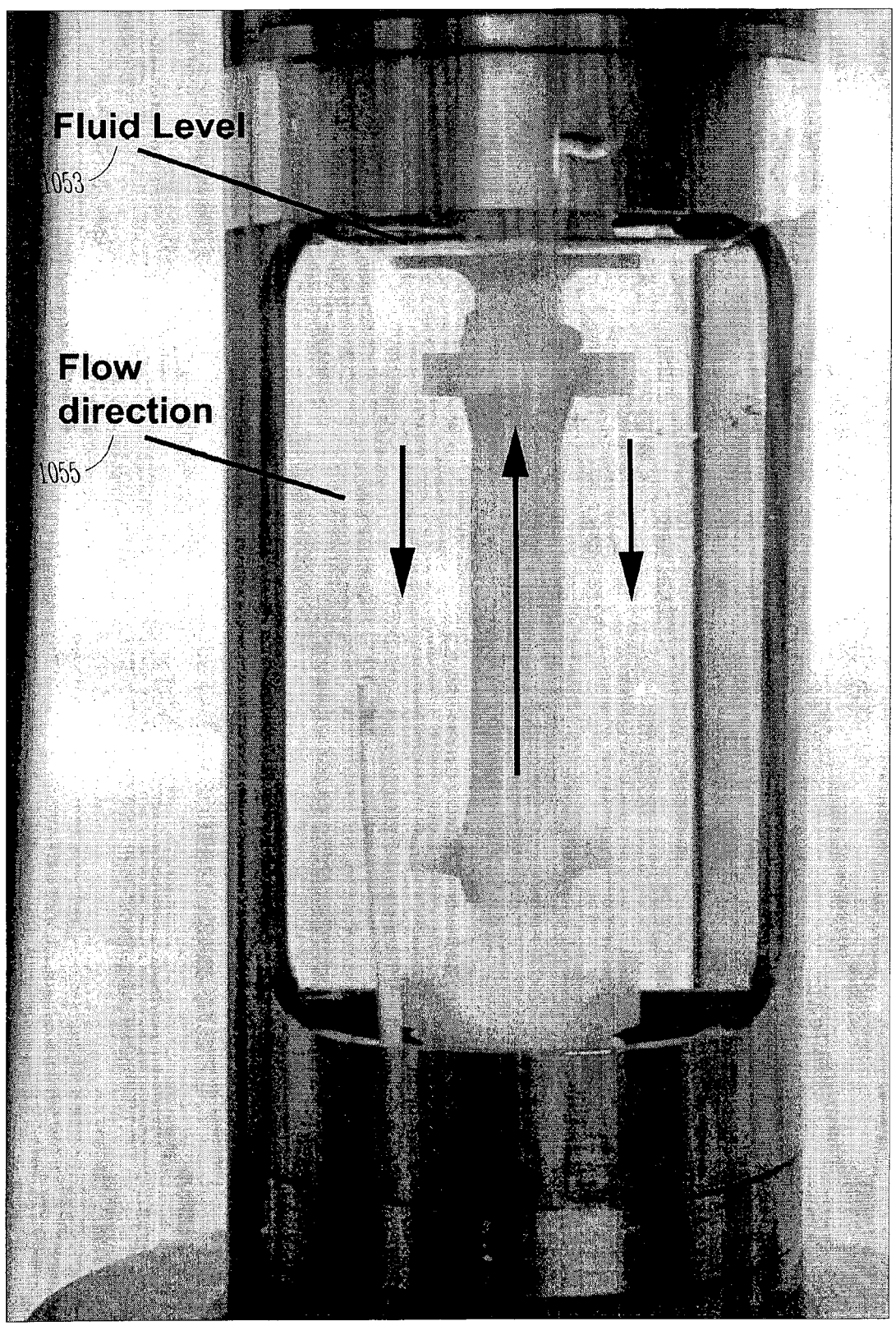

Ports, internal ports 1047-1, 1047-2 and external ports 1049-1, 1049-2 of FIG. 10G, are provided for replenishing nutrients and maintaining the $CO_2$ level of the outer fluid. Also provided are fluid conduits 1071-1, 1071-2 shown FIG. 10D. In one embodiment, fluid conduits 1071-1, 1071-2 are plastic. FIG. 10H shows fluid level 1053 and flow direction 1055. In one embodiment, this is done using a recirculation system. In another embodiment this is performed in a closed system. In one embodiment, the $O_2$ is measured and controlled. In one embodiment, the $O_2$ is only monitored.

It is desirable to measure the local shear stress near the wall so that one can correlate how this affects the endothealization. To accommodate this, feedthroughs 1041-1, 1041-2 for various transducers (pressure, flow, velocity, endoscopes for example) are provided (FIGS. 10D, 10E, and 10F). In one embodiment, transducer 116 in various embodiments represents an ultrasonic Doppler device for measuring the flow velocities from outside the reactor.

In one embodiment, transducer 114 in various embodiments is used to measure the compliance (diametric displacement) of the bioprosthesis 1001 in response to the flow pulses. The compliance signal is coupled to the microprocessor-based controller. The resulting diametric dilation of the bioprosthesis 1001 can be mapped along the bioprosthesis length by means of a precision linear sliding scale linked to the compliance measurement transducer. A signal corresponding to the resulting bioprosthesis dilation is transmitted to the microprocessor-based controller for monitoring and control purposes. By measuring both the applied pressure and diametric displacement the material properties (circumferential/radial stress, normal stress and circumferential/radial strain) are determined in real-time.

Figure 15:
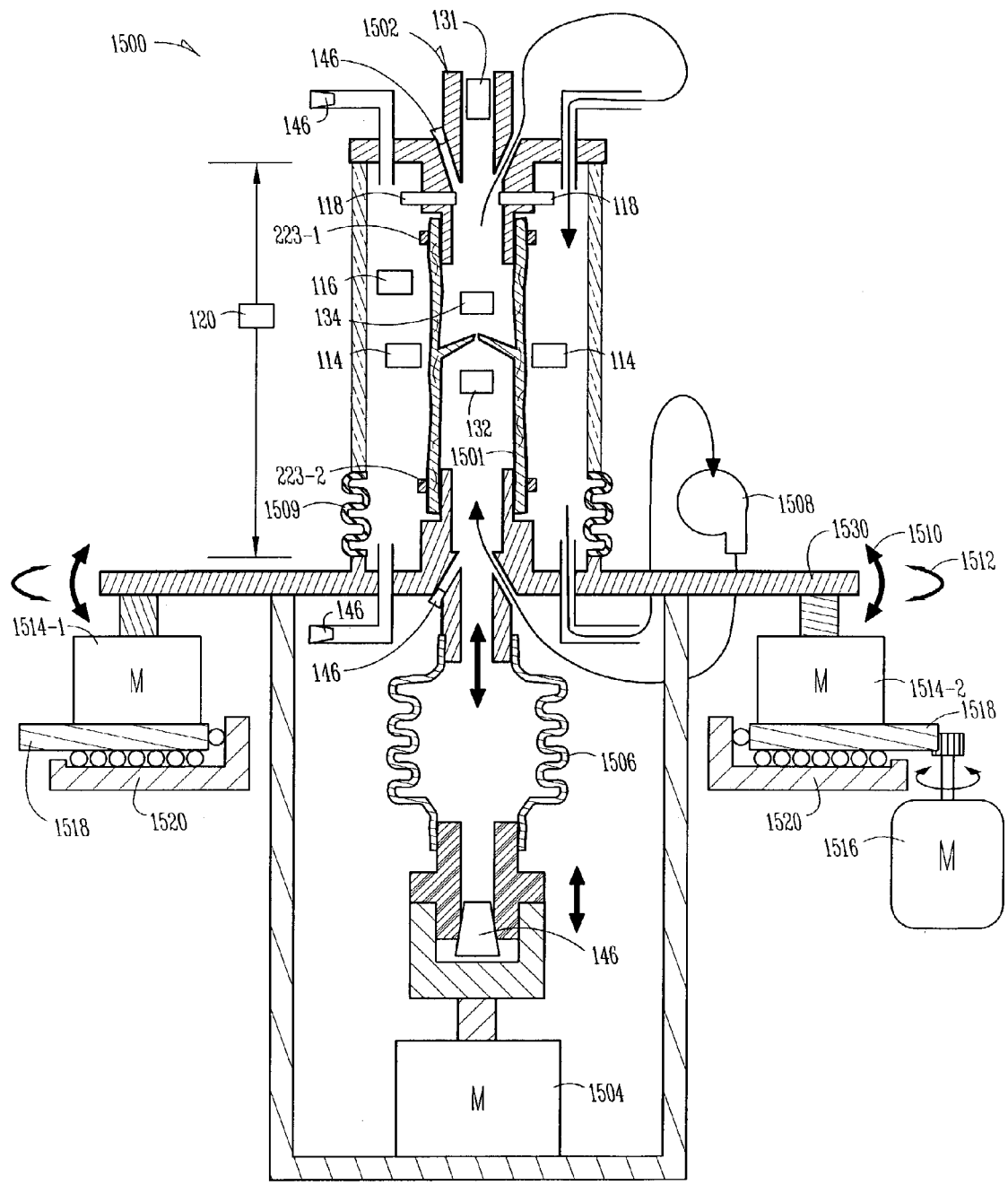
FIG. 15 shows an embodiment of a microprocessor controlled bioreactor providing measurement of axial, bending and torsional loads and displacements of a bioreactor.

In one embodiment, transducer 118 from various embodiments is used to measure the applied axial, bending and torsional load to the bioprosthesis 1001 as a result of the applied flow or as a result of stretching, bending or twisting the lower manifold of the bioreactor. One such example is shown in FIG. 15. In one embodiment, transducer 120 from FIG. 15 is used to measure the applied axial, bending and torsional deflections displacements or stretching of the bioreactor. By measuring both the applied axial, bending, and torsional load and applied axial, bending and torsional displacements the material properties (axial, bending and torsional stress and axial, bending and torsional strain) are determined in real-time.

FIG. 15 shows a bioreactor with flexible joint 1509 which permits axial, bending and torsional motion. In one embodiment, the flexible joint is a flexible plastic. In one embodiment, a flexible rubber is used. Other materials may be used without departing from the present design. The bottom manifold 1530 is extended to permit engagement with linear motors 1514-1 and 1514-2 to provide bending motion 1510 upon actuation of the linear motors. The linear motors are mounted on a platform 1518 which is mated with bearing race 1520. Motor 1516 provides actuation of the bottom manifold 1530 to produce torsional motion 1512. The bending and torsional motion is applied to bioprosthesis 1501 to provide additional degrees of exercise. The sensors may be modified for the additional degrees of freedom in this example. For instance, sensor 120 can measure axial stretch of the top manifold 1502 with respect to the bottom manifold 1530, however, it is understood that the torsional motion may require measurements at particular positions, as for example, with an optical sensor. Such modifications may not be necessary depending on the types of sensors and transducers employed. In one embodiment, a microprocessor is used to control the operations of the various motors to accomplish different motion sequences of the bioreactor.

In one embodiment, during the seeding process pressures P1, P2 and P3 (locations associated with pressure sensors 132, 134, and 136 as demonstrated in FIG. 5) are all equalized. Once the seeding is completed P1 and P2 change in response to the applied flow conditions. These pressures can be measured using catheter pressure transducers 1032 (FIGS. 10C, 10D, 10E, and 10F). The pressures are monitored by the microprocessor-based controller and used as part of the closed loop servo control. The readings can be used for feedback in optimizing the applied flow conditions. P3 can also be measured and controlled and it is expected that it will be primarily a static reading.

In one embodiment, the fixtures use barbed fittings 1025-1, 1025-2 of FIG. 10F with tie wraps 1023 for attachment. In an embodiment, barbed fittings 1025-1, 1025-2 are plastic. In one embodiment, a soft clamping mechanism reduces the stress concentrations at the bioprosthesis ends.

Axial, bending and torsional motion is also beneficial to providing enhanced cell development. This is described as 121 in FIG. 1A and requires the reactor to "stretch, bend or twist".

In one embodiment, during the installation and seeding process, the bioreactor chamber 1002 of FIGS. 10C, 10D is removed from the motorized frame. The bioreactor chamber of FIG. 10A can be disassembled by removing the upper tumbling ring 1033-1 from the upper manifold and sliding the glass tube 1027 off of the inner frame 1029, as shown in FIG. 10F. With the glass tube 1027 removed, the user can change the attachment fittings as needed and install or remove the bioprosthesis matrix. With the bioprosthesis 1001 installed, the glass tube 1027 is fitted over the inner frame 1029. Sealing of the glass tube 1027 is provided by O-rings 1031-1, 1031-2 located at the top and bottom of the frame.

The chamber features tumbling rings 1033-1, 1033-2 (FIGS. 10D, 10E, and 10F) so that the chamber can be rotated about its longitudinal axis for seeding. The tumbling action is provided by a rock polishing tumbler or similar device. In an embodiment, upper tumbling ring 1033-1 is plastic and lower tumbling ring 1033-2 is metal. In another embodiment, tumbling rings 1033-1, 1033-2 are metal. Alternately, tumbling rings 1033-1, 1033-2 are plastic.

Once the bioprosthesis 1001 has been seeded, the reactor is bolted to the crosshead support assembly 1037 of the motorized frame. The crosshead support assembly 1037 is adjusted vertically along the column support 1051 until the bellows pump assembly can be coupled to the linear motor 1004. In an embodiment, the crosshead support assembly 1037 and the column support 1051 are metal. Once the bellows 1006 has been coupled using a motor coupler 1039 as shown in FIGS. 10C, 10D, and 10E, the mean flow pump assembly is also coupled. In an embodiment, motor coupler 1039 is metal coupled to a metal rod from linear motor 1004. In an embodiment, motor coupler 1039 is metal coupled to a split metal sleeve metal rod from linear motor 1004. In an embodiment, motor coupler 1039 is metal coupled to a piece of plastic on which is attached bellows 1006. Transducers are also then inserted as desired and the conditioning is ready to begin. As shown in FIGS. 10D-10G transducers use feedthroughs 1041-1, 1041-2 along with pressure lead 1043.

Measurement of the material properties of the bioprosthesis 1001 while within the bioreactor 1000 provides numerous advantages. The presented systems duplicate conditions found in vivo and create enhanced material properties within the bioprosthesis 1001. The desired material properties include, but are not limited to, the storage and loss modulus of elasticity as a function of applied strain rate or frequency. These are also referred to as the elastic and viscous components of elasticity and are determined from the stress/strain measurements. Other material properties include strength, density, chemistry, temperature and more.

The microprocessor-based controller provides real-time control and monitoring of all of the conditioning factors. It also has been hypothesized that accelerated or super-physiological and retarded or sub-physiological conditions may promote more preferential growth rates at different times in the cell growth process. Controlling conditions in addition to physiological conditions is an advantage of the present system.

The material property measurements can be used to adjust the applied conditions on a real time basis. In one application, the measurements can be used to optimize the applied conditions.

The bioprosthesis collagen matrix is initially very soft and spongy when it is initially placed in the bioreactor. In one embodiment, a soft adjustable clamping means reduces the contact stresses where the bioprosthesis 1001 attaches to the bioreactor 1000. In one embodiment, the clamp is an inflatable cuff or other attachment mechanism.

Various form factors can be achieved using the different teachings provided herein. In one embodiment, an externally mounted gear pump provides mean flow and a linear motor driven bellows pump. In another embodiment, the mean flow and linear motor driven bellows pump are combined within the vessel as depicted in FIG. 3.

Although this description discusses the use of a linear motor 1004 for use with the dynamic pump 1006, it is understood that alternate embodiments may use an alternate motor design. For example, varying embodiments include, but are not limited to, use of a servo motor, a rotary motor, a piezo motor, a servo pneumatic motor, a servo hydraulic motor, a solenoid, a dc brushless motor, a brush type motor, and/or a stepper motor. Other motor embodiments are possible without departing from the scope of the present system.

Figure 11:
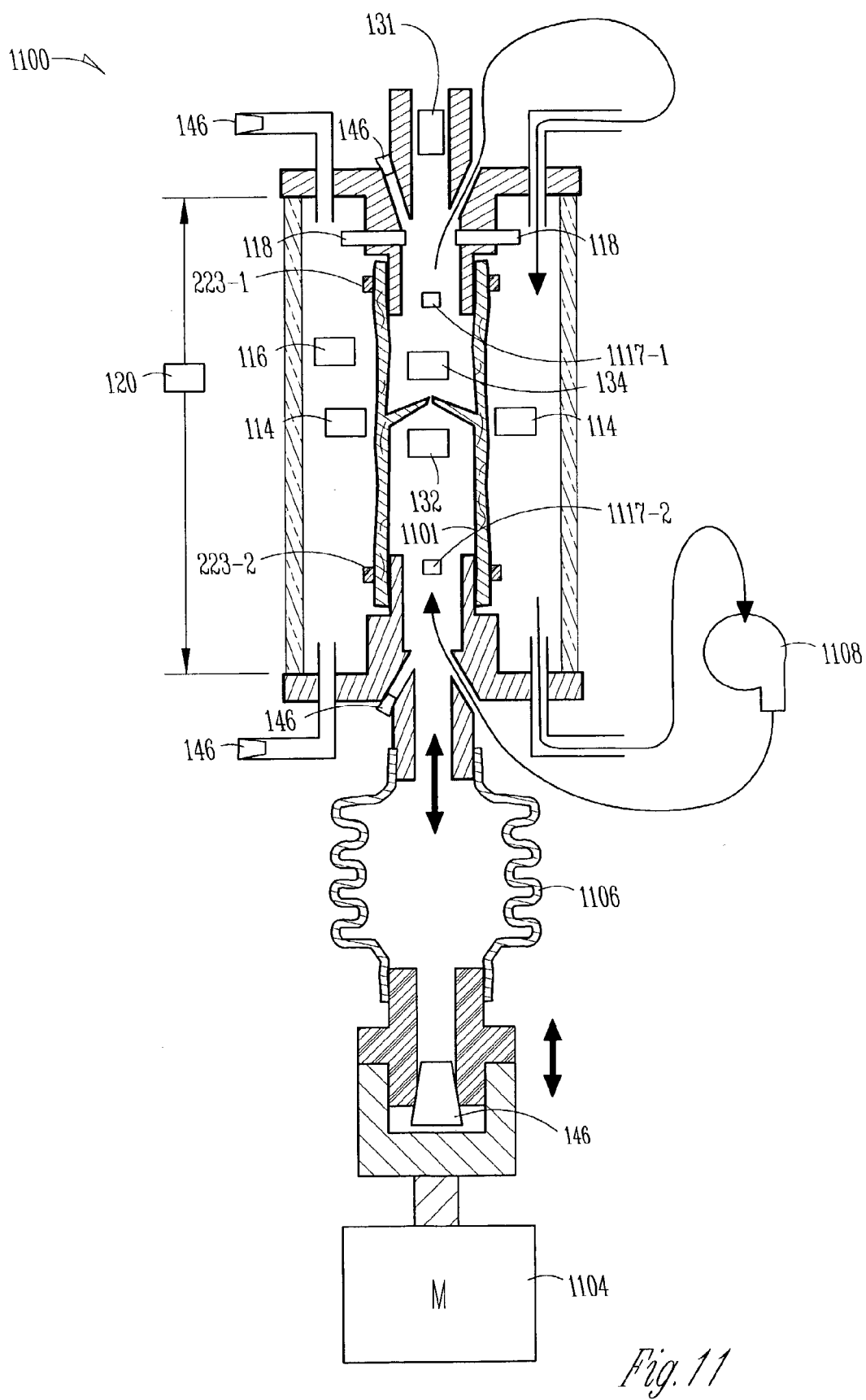
FIG. 11 shows one embodiment of a microprocessor controlled bioreactor with measurement of flow velocities at an input and output of vascular prosthesis inner lumen, according to one embodiment of the present invention.

FIG. 11 shows one embodiment of a microprocessor controlled bioreactor configuration 1100 for measuring flow velocities at an input and output of vascular prosthesis inner lumen. The various embodiments for bioreactor configurations discussed herein can be further enhanced to measure input and output flow velocities. In an embodiment, bioreactor configuration 1100 includes a mean flow pump 1108 and a recirculating design where fluid pressurably introduced into the right hand portion of the bioreactor is transmitted to the central portion of the bioprosthesis 1101 before returning to the mean flow pump 1108. The linear motor 1104 drives the dynamic pump 1106. In this embodiment, tie wraps 223-1, 223-2 as used for bioreactor configuration 200 in FIG. 2 are employed to keep the bioprosthesis 1101 in position. In an embodiment tie wraps 223-1, 223-2 are plastic. It is understood that a soft clamp, as provided in FIG. 1B, may be employed in alternate embodiments of the system. The sensor and monitoring systems mentioned in connection with FIG. 1A are used in varying embodiments of bioreactor configuration 1100 and only some of the possible sensors are shown. Other sensor configurations may be used without departing from the teachings of the present application.

Bioreactor configuration 1100 also includes velocity sensors 1117-1, 1117-2. Velocity sensor 1117-2 measures the flow velocity at the input of bioprosthesis 1101. Velocity sensor 1117-1 measures the flow velocity at the output of bioprosthesis 1101. The two measurements from velocity sensors 1117-1, 1117-2 are used to measure "pseudo" material properties of bioprosthesis 1101. It is believed that if a vascular bioprosthesis 1101 has a high compliance, there will be a substantial phase and amplitude difference between the dynamic velocity readings from velocity sensor 1117-1 and velocity sensor 1117-2.

Figure 12:
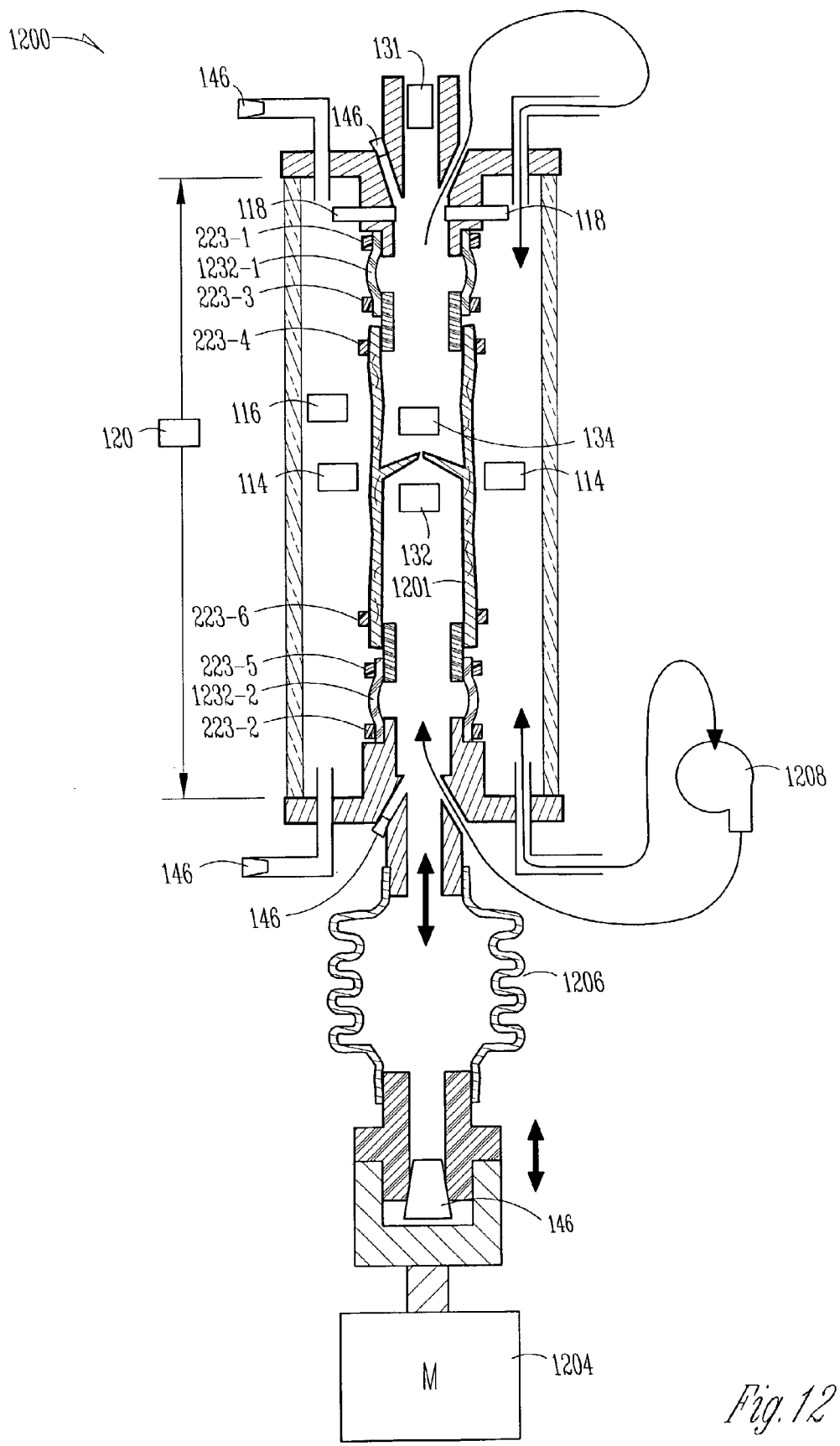
FIG. 12 shows one embodiment of a microprocessor controlled bioreactor using an indirect pressure measurement method, according to one embodiment of the present invention.

FIG. 12 shows one embodiment for a microprocessor controlled bioreactor to provide an indirect pressure measurement method. The various embodiments for bioreactor configurations discussed herein can be further enhanced to measure pressure indirectly. In an embodiment, bioreactor configuration 1200 includes a mean flow pump 1208 and a recirculating design where fluid pressurably introduced into the right hand portion of the bioreactor is transmitted to the central portion of the bioprosthesis 1201 before returning to the mean flow pump 1208. The linear motor 1204 drives the dynamic pump 1206. In this embodiment, tie wraps 223-1, 223-2 as used for bioreactor configuration 200 in FIG. 2 are employed to keep the bioprosthesis 1201 in position. In an embodiment tie wraps 223-1, 223-2 are plastic. It is understood that a soft clamp, as provided in FIG. 1B, may be employed in alternate embodiments of the system. The sensor and monitoring systems mentioned in connection with FIG. 1A are used in varying embodiments of bioreactor configuration 1200 and only some of the possible sensors are shown. Other sensor configurations may be used without departing from the teachings of the present application.

Bioreactor configuration 1200 also includes reference tubes 1232-1, 1232-2, where reference tubes 1232-1, 1232-2 are of a calibrated known compliance. Reference tubes 1232-1, 1232-2 are coupled in series with bioprosthesis 1201 with tie wraps 223-3, 223-4 and 223-5, 223-6, where tie wraps 223-3-223-6 are equivalent to those used in bioreactor configuration 200 of FIG. 2.

By measuring the diametral dilation of the reference tubes 1232-1, 1232-2 using means external to the bioreactor, a measure of the differential pressure applied to bioprosthesis 1201 can be provided. A pressure measurement scheme as used in bioreactor configuration 1200 that is external to the bioreactor may eliminate the need for one or more internal pressure sensors. Such a configuration would enable bioreactor chambers to be built more economically and would also minimize the possibility of contamination from placing catheter pressure transducers within the bioreactor chamber.

Figure 13:
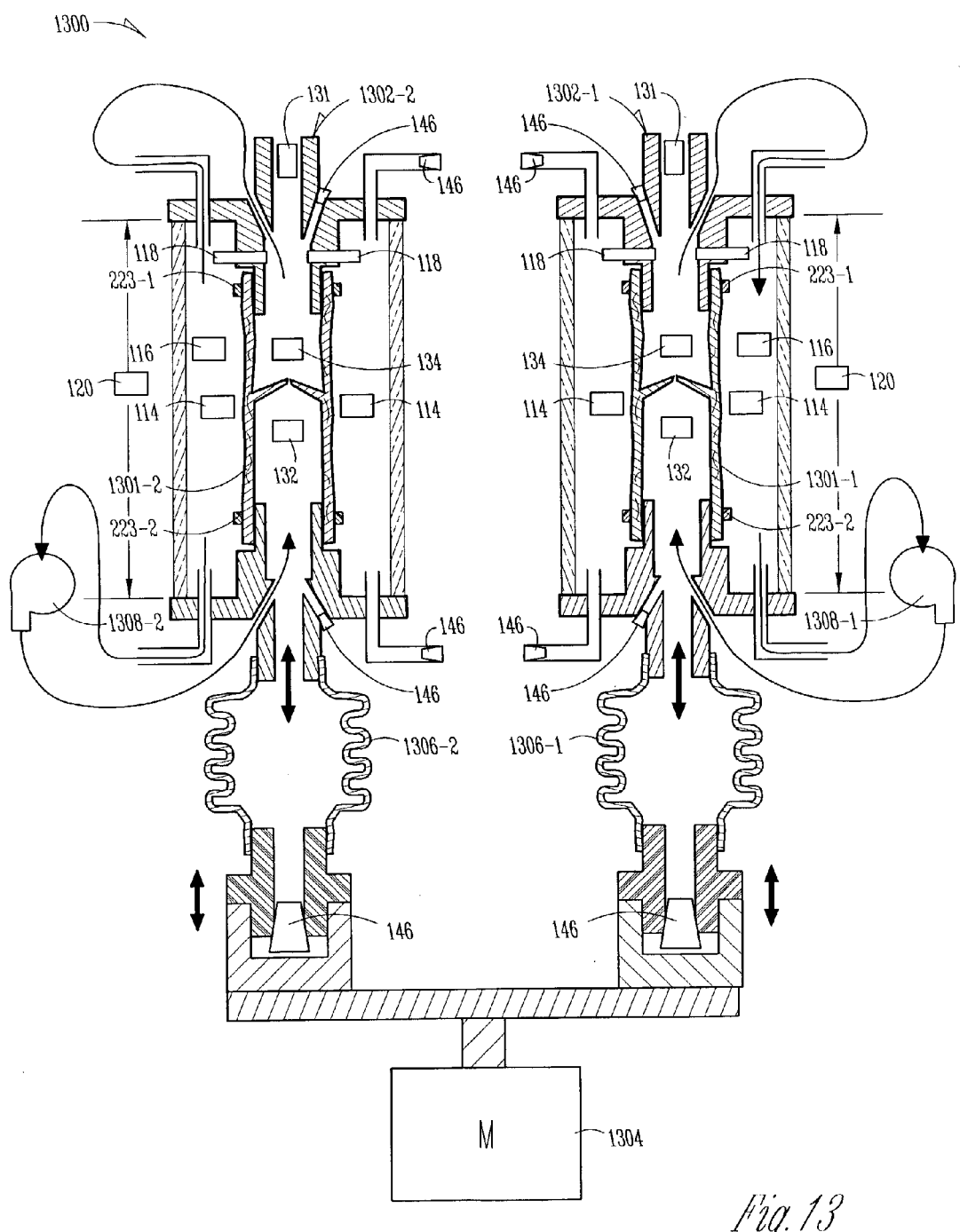
FIG. 13 shows one embodiment of multiple microprocessor controlled bioreactors operating from the same motor, according to one embodiment of the present invention.

FIG. 13 shows a method for operating multiple microprocessor controlled bioreactors operating from the same linear motor. In one embodiment as shown in FIG. 13, bioreactor configuration 1300 includes two microprocessor controlled bioreactors, 1302-1 and 1302-2, operated from the same motor. Bioreactors 1302-1 and 1302-2 can each use one of the various embodiments for a bioreactor configuration as discussed herein. As can be understood by those skilled in the art, multiple microprocessor controlled bioreactors can be operated in accordance with this embodiment.

In an embodiment, bioreactor configuration 1302-1 includes a mean flow pump 1308-1 and a recirculating design where fluid pressurably introduced into the right hand portion of the bioreactor 1302-1 is transmitted to the central portion of the bioprosthesis 1301-1 before returning to the mean flow pump 1308-1. The linear motor 1304 drives the dynamic pump 1306-1. In this embodiment, tie wraps 223-1, 223-2 as used for bioreactor configuration 200 in FIG. 2 are employed to keep the bioprosthesis 1301-1 in position. In an embodiment tie wraps 223-1, 223-2 are plastic. It is understood that a soft clamp, as provided in FIG. 1B, may be employed in alternate embodiments of the system. The sensor and monitoring systems mentioned in connection with FIG. 1A are used in varying embodiments of bioreactor 1302-1 and only some of the possible sensors are shown. Bioreactor 1302-1 can also include the velocity sensors of bioreactor configuration 1100 of FIG. 11 and the pressure measuring reference tubes of bioreactor configuration 1200 of FIG. 12, though for convenience these measurement apparatus are not shown. Other sensor configurations may be used without departing from the teachings of the present application.

In an embodiment, bioreactor configuration 1302-2 includes a mean flow pump 1308-2 and a recirculating design where fluid pressurably introduced into the left hand portion of the bioreactor 1302-2 is transmitted to the central portion of the bioprosthesis 1301-2 before returning to the mean flow pump 1308-2. The linear motor 1304 drives the dynamic pump 1306-2. In this embodiment, tie wraps 223-1, 223-2 as used for bioreactor configuration 200 in FIG. 2 are employed to keep the bioprosthesis 1301-2 in position. In an embodiment tie wraps 223-1, 223-2 are plastic. It is understood that a soft clamp as provided in FIG. 1B may be employed in alternate embodiments of the system. The sensor and monitoring systems mentioned in connection with FIG. 1A are used in varying embodiments of bioreactor 1302-2 and only some of the possible sensors are shown. Bioreactor 1302-2 can also include the velocity sensors of bioreactor configuration 1100 of FIG. 11 and the pressure measuring reference tubes of bioreactor configuration 1200 of FIG. 12, though for convenience these measurement apparatus are not shown. Other sensor configurations may be used without departing from the teachings of the present application.

Operating bioreactor 1302-1 and bioreactor 1302-2 from the same motor 1304 provides an economical configuration. As previously discussed, motor 1304 can be employed in various motor embodiments.

Figure 14:
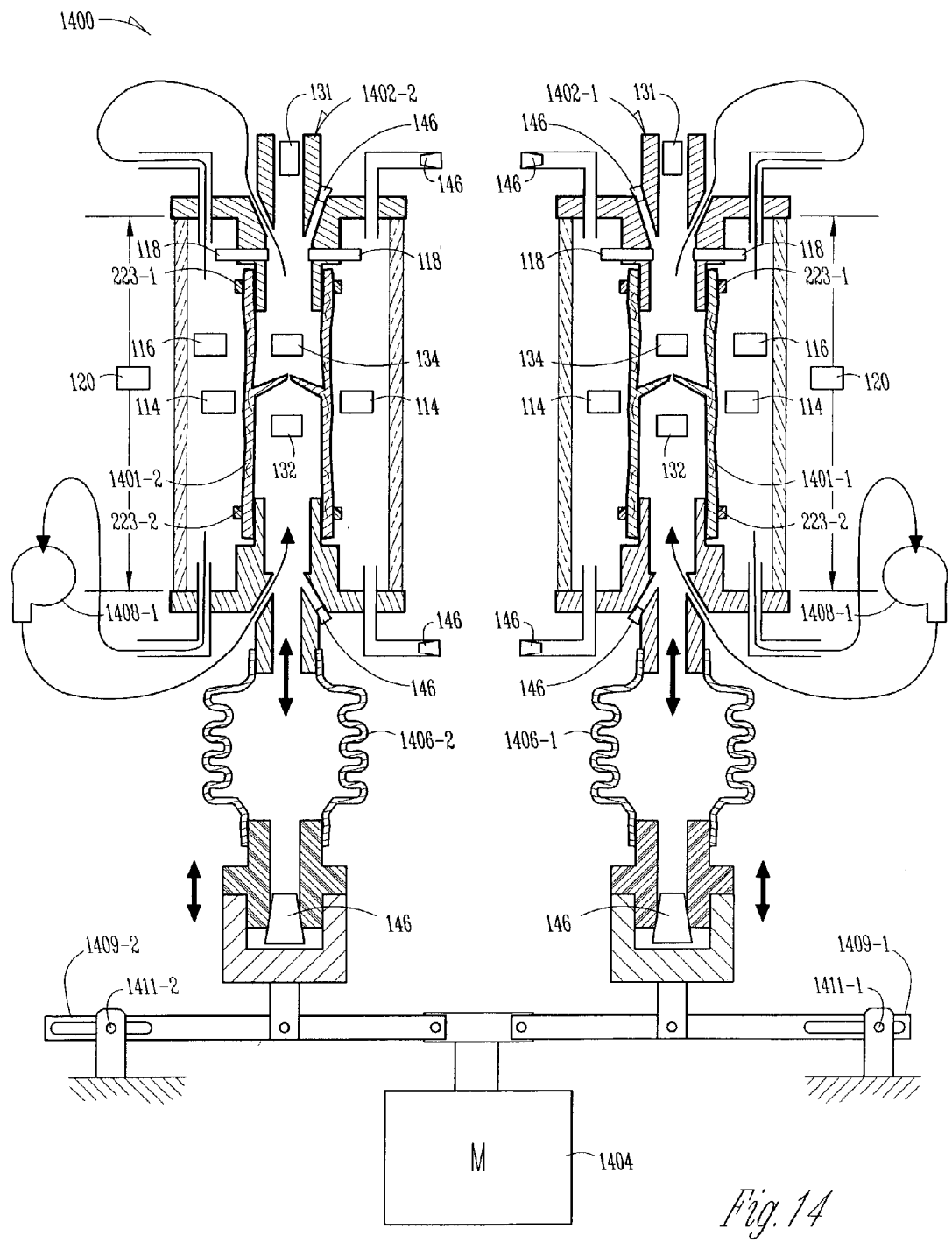
FIG. 14 shows another embodiment of two microprocessor controlled bioreactors operating from the same motor, according to one embodiment of the present invention.

FIG. 14 shows another method for operating multiple microprocessor controlled bioreactors operating from the same linear motor. For convenience, FIG. 14 shows a bioreactor configuration 1400 that includes two microprocessor controlled bioreactors, 1402-1 and 1402-2, operated from the same motor 1404, though more bioreactors can be operated from the same motor 1404. Bioreactors 1402-1 and 1402-2 can each use one of the various embodiments for a bioreactor configuration as discussed herein.

In an embodiment, bioreactor configuration 1402-1 includes a mean flow pump 1408-1 and a recirculating design where fluid pressurably introduced into the right hand portion of the bioreactor 1402-1 is transmitted to the central portion of the bioprosthesis 1401-1 before returning to the mean flow pump 1408-1. The linear motor 1404 drives the dynamic pump 1406-1. In this embodiment, tie wraps 223-1, 223-2 as used for bioreactor configuration 200 in FIG. 2 are employed to keep the bioprosthesis 1401-1 in position. In an embodiment tie wraps 223-1, 223-2 are plastic. It is understood that a soft clamp, as provided in FIG. 1B, may be employed in alternate embodiments of the system. The sensor and monitoring systems mentioned in connection with FIG. 1A are used in varying embodiments of bioreactor 1402-1 and only some of the possible sensors are shown. Bioreactor 1402-1 can also include the velocity sensors of bioreactor configuration 1100 of FIG. 11 and the pressure measuring reference tubes of bioreactor configuration 1200 of FIG. 12, though for convenience these measurement apparatus are not shown. Other sensor configurations may be used without departing from the teachings of the present application.

In an embodiment, bioreactor configuration 1402-2 includes a mean flow pump 1408-2 and a recirculating design where fluid pressurably introduced into the left hand portion of the bioreactor 1402-2 is transmitted to the central portion of the bioprosthesis 1401-2 before returning to the mean flow pump 1308-2. The linear motor 1404 drives the dynamic pump 1406-2. In this embodiment, tie wraps 223-1, 223-2 as used for bioreactor configuration 200 in FIG. 2 are employed to keep the bioprosthesis 1401-2 in position. In an embodiment tie wraps 223-1, 223-2 are plastic. It is understood that a soft clamp, as provided in FIG. 1B, may be employed in alternate embodiments of the system. The sensor and monitoring systems mentioned in connection with FIG. 1A are used in varying embodiments of bioreactor 1402-2 and only some of the possible sensors are shown. Bioreactor 1402-2 can also include the velocity sensors of bioreactor configuration 1100 of FIG. 11 and the pressure measuring reference tubes of bioreactor configuration 1200 of FIG. 12, though for convenience these measurement apparatus are not shown. Other sensor configurations may be used without departing from the teachings of the present application.

In the embodiment shown in FIG. 14, a single linear motor 1404 is used to activate the dynamic pumps 1406-1 and 1406-2 through lever arms 1409-1 and 1409-2, respectively. Lever arm 1409-1 has a movable pivot 1411-1 at one end, and lever arm 1409-1 has a movable pivot 1411-1 at one end. Each movable pivot acts as a moveable cantilever point. This configuration of lever arms and movable pivots enables the dynamic pump displacement for each bioreactor 1402-1 and 1402-2 to be varied. In an alternate embodiment, the hinged points as shown in FIG. 14 for the pivots may be replaced by flexures to avoid any backlash in the pivot points. This bioreactor configuration is not limited to two bioreactors, but may include any number of bioreactors using a single motor and configured as shown in FIG. 14.

Operating multiple bioreactors from the same motor 1404 provides an economical configuration. As previously discussed, linear motor 1404 can be employed using various other motor embodiments.

Other embodiments for bioreactor configurations may include the combination of various elements and configurations as provided throughout these discussions.

The embodiments provided herein are intended to demonstrate some of the embodiments of the present subject matter and to teach a best mode. Variations in structure and design are possible without departing from the scope of the present invention, which is provided by the appended claims and their equivalents.

What is claimed is:

1. A bioreactor for conditioning tissue, comprising:
   a bioreactor chamber, the bioreactor chamber including at least one clamp for holding the tissue;
   a dynamic flow pump for providing dynamic nutrient fluid flow across a surface of the tissue;
   a mean flow pump for providing mean nutrient fluid flow across a surface of the tissue;
   one or more sensors for measuring real time mechanical response of the tissue to conditioning; and
   a microprocessor control for providing real time monitoring and control of sample tissue conditioning, including selective real time adjustment or alteration of mechanical conditioning parameters for the tissue within the bioreactor chamber, wherein the microprocessor control is in communication with the one or more sensors and adapted to selectively programmably adjust or alter conditioning parameters based on variations of the mechanical response and sensed conditions of the tissue and bioreactor conditions as measured by the one or more sensors.

2. The bioreactor of claim 1, wherein at least one clamp is a soft clamp.

3. The bioreactor of claim 1, wherein The dynamic flow pump is a linear motor driven dynamic pump.

4. The bioreactor of claim 1, wherein the dynamic flow pump is a servomotor driven pump.

5. The bioreactor of claim 1, wherein the dynamic flow pump is a voice coil driven dynamic pump.

6. The bioreactor of claim 1, wherein the dynamic flow pump is a piezo-driven dynamic pump.

7. The bioreactor of claim 1, wherein the dynamic flow pump is a stepper motor driven dynamic pump.

8. The bioreactor of claim 1, wherein the dynamic flow pump is a solenoid driven dynamic pump.

9. The bioreactor of claim 1, wherein the dynamic flow pump is a pneumatic driven dynamic pump.

10. The bioreactor of claim 1, wherein the dynamic flow pump is a servohydraulic driven dynamic pump.

11. The bioreactor of claim 1, wherein the dynamic flow pump is a cam driven dynamic pump.

12. The bioreactor of claim 1, wherein the dynamic flow pump is a linear motor driven dynamic pump.

13. The bioreactor of claim 1, wherein the microprocessor control controls at least partially based on inputs from a control software.

14. The bioreactor of claim 1, wherein the microprocessor control includes pressure monitoring means.

15. The bioreactor of claim 1, wherein said one or more sensors include a load sensor and wherein the microprocessor control includes load monitoring and control means.

16. The bioreactor of claim 1, wherein said one or more sensors include a tissue displacement sensor and wherein the microprocessor control includes tissue displacement monitoring and control means.

17. The bioreactor of claim 1, wherein said one or more sensors include a load sensor and wherein the microprocessor control includes tissue stress and strain monitoring and control means.

18. The bioreactor of claim 1, wherein the microprocessor control includes fluid flow monitoring means.

19. The bioreactor of claim 1, wherein the microprocessor control is able to make adjustments to control of conditions for the tissue within the bioreactor chamber using monitored inputs and a program or algorithm that has been programmed into the microprocessor control by the user.

20. The bioreactor of claim 1, further including a first velocity sensor and a second velocity sensor, the first velocity sensor situated in the bioreactor chamber such that it is in-line to an output for the tissue to be conditioned, the second velocity sensor situated in the bioreactor chamber such that it is in-line to an input for the tissue to be conditioned.

21. The bioreactor of claim 1, wherein the first velocity sensor and the second velocity sensor are configured to provide signals to measure flow in the bioreactor at locations configured for the input and output of the tissue to be conditioned.

22. The bioreactor of claim 1, further comprising a second bioreactor chamber having a second mean flow pump and a second dynamic flow pump.

23. The bioreactor of claim 22, wherein the dynamic pump and the second dynamic pump are driven by a linear motor.

24. The bioreactor of claim 23, wherein the linear motor activates the dynamic pump by a lever arm, and the linear motor activates the second dynamic pump by a second lever arm.

25. The bioreactor of claim 24, wherein the lever arm has a movable pivot at one end of the lever arm.

26. The bioreactor of claim 24, wherein the lever arm has a movable pivot at one end of the lever arm, and the second lever arm has a movable pivot at one end of the second lever arm.

27. The bioreactor of claim 24, wherein the lever arm and the second lever arm are coupled to the linear motor by hinged pivots.

28. The bioreactor of claim 1 wherein the dynamic flow pump is a moving magnet driven dynamic pump.

29. The bioreactor of claim 1, wherein the microprocessor control includes linear motor displacement monitoring means.

30. The bioreactor of claim 1 wherein the dynamic flow pump is integrated with the bioreactor chamber.

31. The bioreactor of claim 1 wherein the mean flow pump is integrated with the bioreactor chamber.

32. The bioreactor of claim 1 wherein both the dynamic flow pump and the mean flow pump are integrated with the bioreactor chamber.

33. A bioreactor for conditioning tissue, comprising:
a bioreactor chamber, the bioreactor chamber including at lease one clamp for holding the tissue;
a dynamic flow pump for providing dynamic nutrient fluid flow across a surface of the tissue;
a mean flow pump for providing mean nutrient fluid flow across a surface of the tissue;
one or more sensors for measuring real time response of the tissue to conditioning;
a microprocessor control for providing real time monitoring and control of sample tissue conditioning, including adjustment of conditioning parameters for the tissue within the bioreactor chamber, wherein the microprocessor control is in communication with the one or more sensors and adapted to programmably adjust conditioning parameters based on the mechanical response and variations of sensed conditions of the tissue and bioreactor conditions as measured by the one or more sensors; and
a first reference tube and a second reference tube, the first reference tube coupled to the bioreactor chamber and configured to be coupled to and in-line with one end of the tissue to be conditioned, the second reference tube coupled to the bioreactor chamber and configured to be coupled to and in-line with another end of the tissue to be conditioned.

34. The bioreactor of claim 33, wherein the first and second reference tubes are tubes of calibrated known compliance.

35. The bioreactor of claim 33, wherein the first and second reference tubes are tubes coupled with plastic tie wraps.

36. The bioreactor of claim 33, further including pressure measuring means external to the bioreactor chamber for measuring a diametral dilation of the first and second reference tubes.

37. A bioreactor for treatment of tissue, comprising:
a plurality of ports;
a bioreactor chamber for holding the tissue;
a dynamic flow pump to dynamically pump fluids through or about the tissue;
a mean flow pump to pump fluids through or about the tissue;
a first manifold connected to the chamber at one end and a flexible joint connected to the other end;
a second manifold connected to the flexible joint;
a plurality of linear motors for actuating the second manifold with respect to the first manifold and adapted to controllably impart axial and shearing strain to the tissue;
one or more rotary motors adapted to actuate the second manifold with respect to the first manifold to impart torsional strain to the tissue;
a plurality of sensors for measuring various pressures and temperatures within the bioreactor; and
a control including a microprocessor for controlling fluid flows and motion of the plurality of linear motors and the one or more rotary motors, the control in communication with the plurality of sensors and adapted to programmably adjust a conditioning sequence on a real time basis based on the mechanical response and variations of conditions of the tissue including sensing mechanical conditions and bioreactor conditions as measured by the one or more of the plurality of sensors on a real time basis.

38. The bioreactor of claim 37 wherein the dynamic flow pump is integrated with the bioreactor chamber.

39. The bioreactor of claim 37 wherein both the dynamic flow pump and the mean flow pump are integrated with the bioreactor chamber.

40. A bioreactor for conditioning tissue, comprising:
a bioreactor chamber, the bioreactor chamber including at least one clamp for holding the tissue;
a mean flow pump and a dynamic flow pump to provide dynamic nutrient fluid flow across a surface of the tissue;
microprocessor control means for measuring fluid flow in the bioreactor chamber and for measuring response of the tissue; and
a first reference tube and a second reference tube, the first reference tube coupled to the bioreactor chamber and configured to be coupled to and in-line with one end of the tissue to be conditioned, the second reference tube coupled to the bioreactor chamber and configured to be coupled to and in-line with another end of the tissue to be conditioned,
wherein the microprocessor control means provides real time monitoring and control of conditions for the tissue within the bioreactor chamber.

41. The bioreactor of claim 40, wherein the first and second reference tubes are tubes of calibrated known compliance.

42. The bioreactor of claim 40, wherein the first and second reference tubes are tubes coupled with plastic tie wraps.

43. The bioreactor of claim 40, further including pressure measuring means external to the bioreactor chamber for measuring a diametral dilation of the first and reference tubes.

* * * * *